US012005174B2

(12) United States Patent
Crnkovich et al.

(10) Patent No.: US 12,005,174 B2
(45) Date of Patent: Jun. 11, 2024

(54) AUTOMATIC PRIMING AND SCHEDULING FOR DIALYSIS SYSTEMS

(71) Applicant: Fresenius Medical Care Holdings, Inc., Waltham, MA (US)

(72) Inventors: Martin Joseph Crnkovich, Walnut Creek, CA (US); David Yuds, Hudson, NH (US); Fei Wang, Concord, CA (US); Haiyong Wang, Pleasanton, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 647 days.

(21) Appl. No.: 16/009,810

(22) Filed: Jun. 15, 2018

(65) Prior Publication Data

US 2019/0381232 A1    Dec. 19, 2019

(51) Int. Cl.
*A61M 1/36* (2006.01)
*A61M 39/28* (2006.01)
*G16H 40/63* (2018.01)

(52) U.S. Cl.
CPC ........ *A61M 1/3644* (2014.02); *A61M 1/3647* (2014.02); *A61M 1/365* (2014.02);
(Continued)

(58) Field of Classification Search
CPC ........ A61M 1/16; A61M 1/34; A61M 1/3643; A61M 1/3644; A61M 1/3647; A61M 1/365; A61M 2205/15; A61M 2205/18; A61M 2205/3306; A61M 2205/3317; A61M 2205/3331; A61M 2205/3334; A61M 2205/3368; A61M 2205/3389; A61M 2205/502; A61M 2205/505; A61M 2205/581; A61M 2205/582; A61M 2205/583; A61M 2205/584; A61M 2205/587; A61M 2205/702; A61M 2205/8206; A61M 39/28; A61M 1/1656;
(Continued)

(56) References Cited

U.S. PATENT DOCUMENTS 5,326,476 A * 7/1994 Grogan ................. G16H 20/17
                                                        210/646
5,674,404 A * 10/1997 Kenley .................... A61L 2/04
                                                        210/741
(Continued)

FOREIGN PATENT DOCUMENTS

WO    WO 94/11093    5/1994
WO    WO 96/25214    8/1996

OTHER PUBLICATIONS

Dialog, Dialysis Machine, 2016, p. 218-252 (Year: 2016).*
(Continued)

*Primary Examiner* — Jonathan M Peo
(74) *Attorney, Agent, or Firm* — Fish & Richardson P.C.

(57) ABSTRACT

A method including automatically performing at least one integrity test on a dialysis machine after powering on the dialysis machine, wherein the at least one integrity test is selected from the group consisting of a battery test, a dialysate conductivity test, and a dialysate temperature test. The method also includes presenting, on a display of the dialysis machine, a first set of instructions for priming the dialysis machine after completing the at least one integrity test.

16 Claims, 14 Drawing Sheets

(52) U.S. Cl.
CPC .............. *G16H 40/63* (2018.01); *A61M 39/28* (2013.01); *A61M 2205/15* (2013.01); *A61M 2205/18* (2013.01); *A61M 2205/3306* (2013.01); *A61M 2205/3317* (2013.01); *A61M 2205/3331* (2013.01); *A61M 2205/3334* (2013.01); *A61M 2205/3368* (2013.01); *A61M 2205/3389* (2013.01); *A61M 2205/505* (2013.01); *A61M 2205/581* (2013.01); *A61M 2205/582* (2013.01); *A61M 2205/583* (2013.01); *A61M 2205/584* (2013.01); *A61M 2205/587* (2013.01); *A61M 2205/702* (2013.01); *A61M 2205/8206* (2013.01)

(58) Field of Classification Search
CPC .... A61M 1/1613; A61M 1/169; A61M 1/341; A61M 1/3626; A61M 1/3646; A61M 2205/3324; A61M 2205/52; A61M 1/1601; A61M 1/1607; A61M 1/166; A61M 1/1668; A61M 1/1682; A61M 1/1694; A61M 2205/12; A61M 1/1621; A61M 1/1635; A61M 1/1639; A61M 1/165; A61M 1/1662; A61M 1/1664; A61M 1/1666; A61M 1/1672; A61M 1/168; A61M 1/1688; A61M 1/1692; A61M 1/1696; A61M 1/267; A61M 1/3427; A61M 1/3434; A61M 1/3437; A61M 1/3441; A61M 1/3451; A61M 1/3465; A61M 1/3468; A61M 1/3627; A61M 1/3652; A61M 1/3672; A61M 2039/1005; A61M 2205/13; A61M 2205/3313; A61M 2205/3344; A61M 2205/3379; A61M 2205/3393; A61M 2205/705; A61M 1/1619; A61M 1/1629; A61M 1/1633; A61M 1/1643; A61M 1/1658; A61M 1/167; A61M 1/1686; A61M 1/28; A61M 1/284; A61M 1/288; A61M 1/3403; A61M 1/3413; A61M 1/3417; A61M 1/342; A61M 1/3431; A61M 1/3444; A61M 1/3458; A61M 1/3462; A61M 1/3472; A61M 1/3486; A61M 1/36; A61M 1/3606; A61M 1/3607; A61M 1/3609; A61M 1/3621; A61M 1/3624; A61M 1/3649; A61M 1/3656; A61M 1/3666; A61M 1/3667; A61M 2202/0413; A61M 2205/123; A61M 2205/128; A61M 2205/276; A61M 2205/3327; A61M 2205/3337; A61M 2205/3553; A61M 2205/3561; A61M 2205/3584; A61M 2205/50; A61M 2205/75; A61M 2209/082; A61M 2209/084; A61M 5/172; A61M 60/113; A61M 60/205; A61M 60/258; A61M 60/268; A61M 60/279; A61M 60/43; A61M 60/50; A61M 1/14; G16H 40/63; G16H 20/40; G16H 20/17; Y10S 210/929; Y10S 261/28; G06F 3/0482; G06F 3/04847; G06F 3/0488; G06F 19/00; G06F 19/3468; A61L 2/022; A61L 2/28; C02F 11/04; C07K 14/4711; C07K 16/40; C12N 9/6421; G01N 33/573; G01N 33/6896; Y10T 137/87893

See application file for complete search history.

(56) References Cited

U.S. PATENT DOCUMENTS

| | | | | |
|---|---|---|---|---|
| 5,776,345 | A  * | 7/1998  | Truitt  | A61M 1/16 210/134 |
| 6,406,426 | B1 * | 6/2002  | Reuss  | A61B 5/002 128/920 |
| 6,758,975 | B2   | 7/2004  | Piedmont | |
| 2004/0195178 | A1 * | 10/2004 | Carpenter  | A61M 1/3667 210/645 |
| 2011/0092894 | A1 * | 4/2011  | McGill  | A61M 1/1522 604/151 |
| 2012/0138533 | A1 * | 6/2012  | Curtis  | A61M 1/16 210/646 |
| 2013/0165847 | A1 * | 6/2013  | Scarpaci  | A61M 60/113 417/478 |
| 2013/0304020 | A1 * | 11/2013 | Wilt  | A61M 5/172 604/506 |
| 2017/0028120 | A1   | 2/2017  | Kelly et al. | |
| 2017/0266360 | A1 * | 9/2017  | Burbank  | A61M 1/14 |
| 2018/0169314 | A1 * | 6/2018  | Gassman  | A61M 5/14 |
| 2021/0220502 | A1 * | 7/2021  | Bardorz  | G16H 40/63 |

OTHER PUBLICATIONS

International Search Report and Written Opinion in Application No. PCT/US2019/036943, dated Nov. 4, 2019, 22 pages.

PCT International Preliminary Report on Patentability in International Appln. No. PCT/US2019/036943, dated Dec. 24, 2020, 15 pages.

* cited by examiner

AUTOMATIC PRIMING AND SCHEDULING FOR DIALYSIS SYSTEMS

TECHNICAL FIELD

This specification relates generally to automatic priming and scheduling for dialysis systems.

BACKGROUND

Dialysis is a treatment used to support a patient with insufficient renal function. The two principal dialysis methods are hemodialysis and peritoneal dialysis. During hemodialysis, the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

Before performing a hemodialysis treatment, disposable bloodline sets of hemodialysis systems are typically first primed with a sterile solution. The sterile solution can be recirculated within a bloodline set to fully remove air from the bloodline set before a patient's blood is run through the bloodline set.

SUMMARY

In one aspect, a method includes automatically performing at least one integrity test on a dialysis machine after powering on the dialysis machine, wherein the at least one integrity test is selected from the group consisting of a battery test, a dialysate conductivity test, and a dialysate temperature test. The method also includes presenting, on a display of the dialysis machine, a first set of instructions for priming the dialysis machine after completing the at least one integrity test.

In some implementations, the method includes presenting, on the display, an instruction including flowing, using gravity, priming fluid from a fluid source through an arterial blood line set. In some cases, the method includes presenting on the display, an instruction including closing an end of the arterial blood line set and pumping the priming fluid through a dialyzer to prime the dialyzer. In some cases, the method includes presenting, on the display, an instruction including priming a dialysate side of a dialyzer of the dialysis machine prior to priming the arterial blood line set.

In some implementations, the method includes presenting, on the display of the dialysis machine, a second set of instructions for priming the dialysis machine upon completion of the first set of instructions. In some cases, completion of the first set of instructions includes running a predetermined volume of fluid through a blood pump. In some cases, the second set of instructions is a set of instructions for a recirculation portion of an automatic priming procedure. In some cases, the second set of instructions instructs a user to connect the arterial blood line set to the venous blood line set. In some cases, one instruction in the second set of instructions instructs a user to rotate the dialyzer.

In some cases, the method includes performing at least one functionality test during the recirculation portion of the automatic priming procedure. In some cases, the first set of instructions is displayed on a first screen and wherein the second set of instructions is displayed on a second screen, the second screen replacing the first screen when the first set of instructions is completed. In some cases, at least one of the first screen and the second screen includes a progress bar for indicating the progress of the priming process. In some cases, at least one functionality test is selected from the group consisting of a positive pressure test, a negative pressure test, an optical detection test, a blood leak detection test, a level detection test, a transmembrane pressure test, a venous pressure test, and an arterial pressure test. In some cases, performing at least one functionality test includes measuring at least one parameter associated with the at least one functionality test, comparing, by a controller, the at least one parameter to an expected operating range for the at least one parameter, if the at least one parameter is outside of the expected operating range, returning an error message on the display, and if the at least one parameter is within the expected operating range, indicating, on the display, that the at least one functionality test has been passed. In some cases, the error message includes a description of a problem with at least one component of the dialysis machine.

In some implementations, the method includes presenting, on the display, a graphical representation of the dialysis machine. In some cases, the graphical representation of the dialysis machine and the first set of instructions include labels indicating that a step in the first set of instructions including the label should be performed on a component of the dialysis machine including the label.

In another aspect, a method of operating a dialysis machine includes automatically powering on the dialysis machine at a pre-set time on a selected day, automatically performing at least one integrity test on the dialysis machine after automatically powering on the dialysis machine, wherein the at least one integrity test is selected from the group consisting of a battery test, a dialysate conductivity test, and a dialysate temperature test, and presenting, on a display of the dialysis machine, a first set of instructions for priming the dialysis machine after completing the at least one integrity test.

In some implementations, the pre-set time is selected via a scheduling interface of the dialysis machine.

In some implementations, the method includes automatically sending the dialysis machine into a low power mode after a predetermined time interval has passed without user interaction with the dialysis machine.

In some implementations, the method includes emitting an alert prior to automatically powering on the dialysis machine. In some cases, the alert is an auditory alert, a visual alert, and/or a vibratory alert. In some cases, emitting the alert includes displaying the alert on a user interface of the dialysis machine and providing an option on the user interface to abort the powering on of the dialysis machine.

In some implementations, the method includes delivering a first current to one or more first components of the dialysis machine prior to automatically powering on the dialysis machine, the first current being less than a current used to automatically power on the dialysis machine. In some cases, the one or more first components include a sensor and a controller, the sensor being configured to detect a condition related to the dialysis machine and the controller being configured to use data related to the detected condition to commence the automatically powering on of the dialysis machine. In some cases, the sensor is configured to detect whether a panel for enclosing internal components of the dialysis machine is closed, and the controller is configured to commence the automatically powering on of the dialysis machine after determining, based on data received from the sensor, that the panel is closed.

In another aspect, a method of operating a dialysis machine includes emitting an alert to indicate that the dialysis machine is to be powered on and then automatically powering on the dialysis machine.

In some implementations, the alert is an auditory alert, a visual alert, and/or a vibratory alert.

In some implementations, emitting the alert includes displaying the alert on a user interface of the dialysis machine and providing an option on the user interface to abort the powering on of the dialysis machine.

In some implementations, the method includes delivering a first current to one or more first components of the dialysis machine prior to automatically powering on the dialysis machine, the first current being less than a current used to automatically power on the dialysis machine. In some cases, the one or more first components include a sensor and a controller, the sensor being configured to detect a condition related to the dialysis machine and the controller being configured to use data related to the detected condition to commence the automatically powering on of the dialysis machine. In some cases, the sensor is configured to detect whether a panel for enclosing internal components of the dialysis machine is closed, and the controller is configured to commence the automatically powering on of the dialysis machine after determining, based on data received from the sensor, that the panel is closed.

In another aspect, a dialysis system includes a computing device. The computing device includes a memory configured to store instructions and a processor to execute the instructions to perform operations. The operations include automatically performing at least one integrity test on a dialysis machine after powering on the dialysis machine, wherein the at least one integrity test is selected from the group consisting of a battery test, a dialysate conductivity test, and a dialysate temperature test and presenting, on a display of the dialysis machine, a first set of instructions for priming the dialysis machine after completing the at least one integrity test.

In another aspect, a dialysis system includes a computing device. The computing device includes a memory configured to store instructions and a processor to execute the instructions to perform operations. The operations include automatically powering on a dialysis machine at a pre-set time on a selected day, automatically performing at least one integrity test on the dialysis machine after automatically powering on the dialysis machine, wherein the at least one integrity test is selected from the group consisting of a battery test, a dialysate conductivity test, and a dialysate temperature test, and presenting, on a display of the dialysis machine, a first set of instructions for priming the dialysis machine after completing the at least one integrity test.

In another aspect, a dialysis system includes a computing device including a memory configured to store instructions and a processor to execute the instructions to perform operations. The operations include emitting an alert to indicate that a dialysis machine is to be powered on, and then automatically powering on the dialysis machine. Implementations can include one or more of the following advantages.

In certain implementations, an automatic priming procedure limits the number of steps in a priming process and limits the number of instances in which a user needs to interact with a dialysis machine to complete a priming procedure. In certain implementations, all of the instructions that a user needs to prime the dialysis machine are located on two screens. The limited number of steps required eliminates a need for a user to thumb through a manual to find setup instructions and change their gloves between setup steps.

In certain implementations, the dialysis machine automatically performs multiple integrity tests, including a level detector test, an arterial pressure test, a venous pressure test, and a transmembrane pressure test before or during the automatic priming procedure. With the integrity tests being run automatically, the dialysis machine setup is simpler and more efficient, thereby allowing a dialysis treatment to begin more quickly after a user arrives at the dialysis machine.

In certain implementations, during the automatic priming process, the dialysate side of the dialyzer is filled with priming solution before the blood side of the dialyzer. Filling the dialysate side of the dialyzer first significantly reduces the amount of air in the dialyzer after priming is complete. Because less air is present, the priming process used to remove the air from the dialyzer may be completed more quickly. In certain implementations, no tapping on the dialyzer to remove air is required.

In certain implementations, the dialysis machine includes an automatic power on procedure in which the dialysis machine may be programmed to automatically power on at a given time. The programmed power on times may vary by day of the week. The automatic power on procedure may be coupled with the automatic priming procedure so that a dialysis machine running both of these procedures could be powered on and ready for user interaction before a user arrives at a dialysis clinic. In contrast, many prior dialysis machines required the user to power on the machine, which required the user to arrive at the machine well before a planned treatment.

In some implementations, an alert is emitted by the dialysis machine prior to commencing the automatic powering on process. The alert can serve as a warning to personnel in the vicinity of the dialysis machine to move away from the dialysis machine to ensure that they are not touching movable parts, such as pumps and clamps, or electrically charged parts of the dialysis machine.

Other aspects, features, and advantages will be apparent from the description and drawings, and from the claims.

DETAILED DESCRIPTION

Figure 1A:
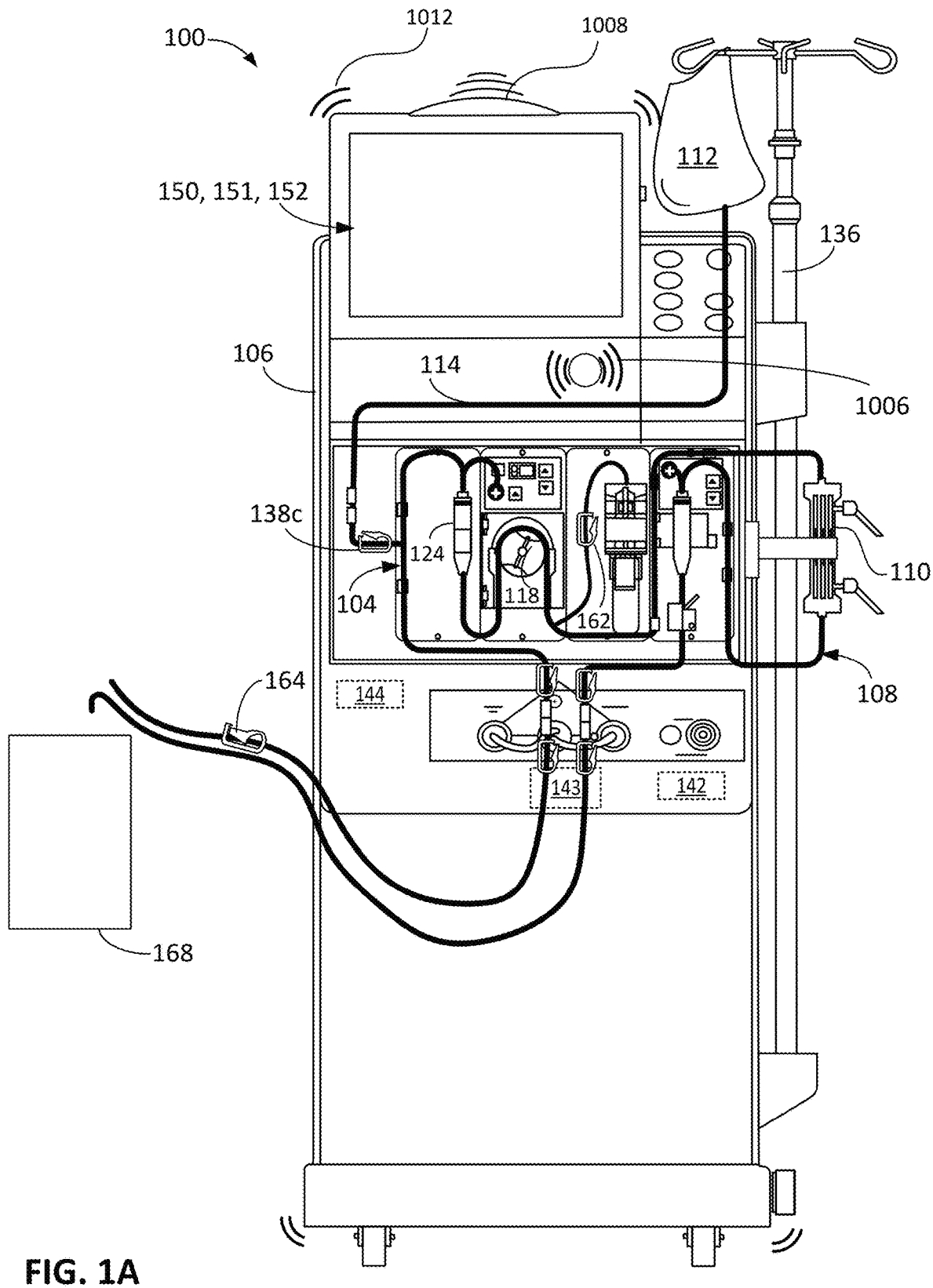
FIG. 1A is a schematic of a hemodialysis system that includes a fluid line set secured to a hemodialysis machine and that is configured for an automatic priming procedure.

Referring to FIG. 1A, a hemodialysis system 100 includes a hemodialysis machine 106 to which a blood line set including an arterial line set 104, a venous line set 108, and a dialyzer 110 is connected. Before connecting the arterial line set 104 and the venous line set 108 to the patient, the blood line set is typically primed with a priming solution, such as saline, to remove air from the arterial and venous line sets 104, 108, the dialyzer 110, and other components of the blood line set. FIG. 1A shows the hemodialysis system 100 in a priming configuration in which the arterial line set 104 and the venous line set 108 are connected to a waste container 168. A supply line 114 is connected at one end to a saline bag 112 and at the other end to the arterial line set 104.

The hemodialysis machine 106, as will be described in greater detail below, is configured to automatically carry out at least a portion of a priming procedure. Additionally, a user interface system 150 of the hemodialysis machine 106 provides the user with detailed information required to carry out the priming procedure. During the priming procedure, the hemodialysis machine 106 is operated to circulate saline from the saline bag 112 through the blood line set to remove air from the blood line set. The saline and air entrapped therein is then sent to the waste container 168 for disposal.

Figure 1B:
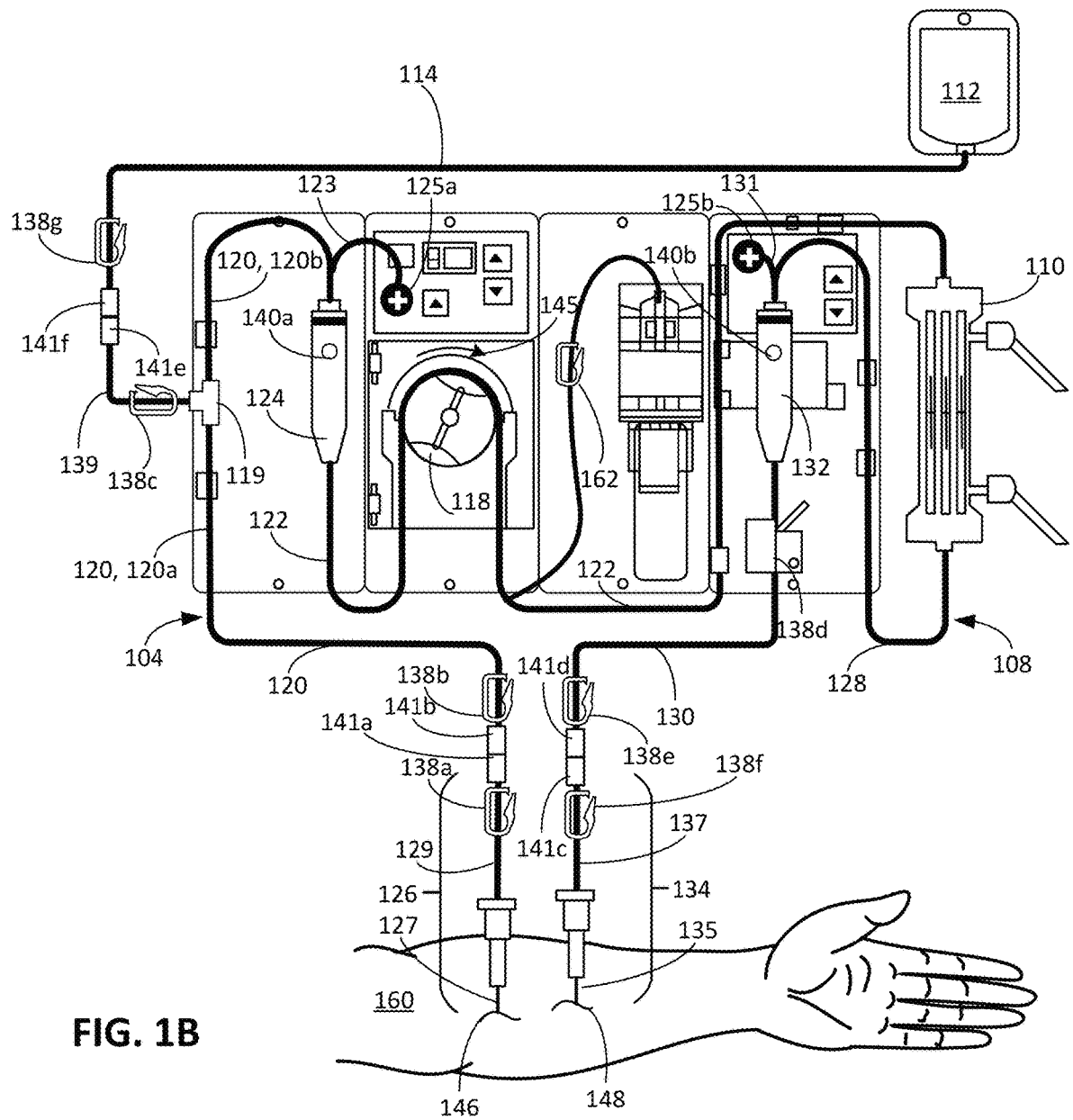
FIG. 1B is a close-up view of the hemodialysis system of FIG. 1A during an extracorporeal treatment of a patient.

Referring to FIG. 1B, after priming is complete, the user connects the arterial and venous line sets 104, 108 to a patient, and the hemodialysis machine 106 runs in a treatment mode to perform a hemodialysis treatment on the patient. During the hemodialysis treatment, the patient's blood is passed through one chamber of the dialyzer 110 while a dialysis solution or dialysate is passed through another chamber of the dialyzer 110. A semi-permeable membrane in the dialyzer 110 separates the blood from the dialysate within the dialyzer 110 and allows diffusion and osmosis exchanges to take place between the dialysate and the blood. These exchanges across the membrane result in the removal of waste products, including solutes like urea and creatinine, from the blood. These exchanges also regulate the levels of other substances, such as sodium and water, in the blood.

Still referring to FIG. 1B, the arterial line set 104 includes an arterial access line 120, an arterial line 122, and an arterial drip chamber 124. One end of the arterial access line 120 is connected to the top of the arterial drip chamber 124, and the other end of the arterial access line 120 is connectable to an arterial needle assembly 126. The arterial access line 120 includes a first portion 120a and a second portion 120b each connected to a fluid adapter 119 of the arterial line set 104. The arterial line 122 extends from the bottom of the arterial drip chamber 124 to the dialyzer 110.

The arterial drip chamber 124 is positioned along the arterial access line 120. A pressure transducer 125a is connected to the arterial drip chamber 124 via a pigtail line 123 extending from the arterial drip chamber 124 and is configured to detect a fluid pressure within the arterial drip chamber 124.

The arterial needle assembly 126 includes a needle 127 that is insertable into the patient 160 and a fluid line 129 that is connectable to the arterial access line 120. A manually operable connector 141a at the end of the fluid line 129 is configured to be connected to a manually operable connector 141b at the end of the first portion 120a of the arterial access line 120. Like the arterial line set 104, the arterial needle assembly 126 can be a single-use disposable component that is discarded after the end of the extracorporeal treatment. During a hemodialysis treatment, the arterial needle assembly 126 is connected to the arterial access line 120 using the connectors 141a, 141b, and the needle 127 of the arterial needle assembly 126 is inserted into the patient 160 to enable blood to be drawn into the arterial line set 104 from the patient 160.

The venous line set 108 includes a venous line 128, a venous access line 130, and a venous drip chamber 132. The venous line 128 extends from the dialyzer 110 to the top of the venous drip chamber 132. One end of the venous access line 130 is connected to a bottom of the venous drip chamber 132, and the other end of the venous access line 130 is connected to a venous needle assembly 134. A pressure transducer 125b is connected to the venous drip chamber 132 via a pigtail line 131 extending from the venous drip chamber 132 and is configured to detect a fluid pressure within the venous drip chamber 132.

During a hemodialysis treatment, the venous needle assembly 134 is connected to the venous access line 130. The venous needle assembly 134 includes a needle 135 that is insertable into the patient 160 to enable filtered blood, e.g., blood that has travelled through the dialyzer 110, to be returned to the patient 160 through the venous line set 108. The venous needle assembly 134 further includes a fluid line 137 to be connected to the venous access line 130. A manually operable connector 141c at the end of the fluid line 137 is configured to be connected to a manually operable connector 141d at the end of the venous access line 130.

The arterial line set 104, the venous line set 108, and the dialyzer 110 form an extracorporeal blood circuit through which the blood of the patient 160 circulates during treatment. A blood pump 118, when operated during the hemodialysis treatment, causes blood to flow from the patient 160, through the extracorporeal blood circuit, and then back into the patient 160 after filtration has occurred in the dialyzer 110. The blood pump 118 generates a negative pressure in the arterial access line 120, the arterial drip chamber 124, and the portion of the arterial line 122 upstream of the blood pump 118. A signal generated by the pressure transducer 125a can be indicative of this negative pressure. The blood pump 118 generates a positive pressure in the portion of the arterial line 122 downstream of the blood pump 118 and in the venous line set 108. A signal generated by the pressure transducer 125b can be indicative of the positive pressure in the downstream portion of the arterial line 122 and the venous line set 108.

Another disposable portion of the hemodialysis system 100 includes the fluid line 114 and the saline source 112. The fluid line 114 is connected to the arterial line set 104 along the arterial access line 120. Specifically, a port 139 extends from the fluid adapter 119 of the arterial line set 104 and is connectable to the saline source 112, e.g., through the fluid line 114. An end of the port 139 includes a manually operable connector 141e configured to be connected to a manually operable connector 141f at an end of the fluid line 114. The connectors 141a-141f described herein can be threaded connectors that connect to one another through a threaded engagement, a snap fit engagement, or another appropriate engagement mechanism.

The fluid line 114 is connected to the saline bag 112 such that saline from the saline bag 112 can be drawn or forced into the arterial line set 104 when the fluid line 114 is connected to the port 139 of the arterial line set 104. The saline bag 112 can be hung from a vertically extending member 136 (shown in FIG. 1A) that positions the saline bag 112 above the patient 160. As a result, flow of saline from the saline bag 112 to the patient 160, e.g., through the arterial line set 104, can be driven by gravity.

The hemodialysis machine 106 further includes flow regulators engageable with the arterial line set 104, the venous line set 108, and the fluid line 114. The hemodialysis machine 106 of FIG. 1B includes clamps 138a-138g as flow regulators. In the illustrated embodiment, the clamps 138a-138f are manually operable and the clamp 138d is automated. The clamp 138a is positioned to engage the fluid line 129 of the arterial needle assembly 126. The clamp 138b is positioned to engage the arterial access line 120. The clamp 138c is positioned to engage the port 139 extending from the fluid adapter 119 of the arterial line set 104. The clamp 138d is positioned to engage the portion of the venous access line 130 proximate the venous drip chamber 132. The clamp 138e is positioned to engage the portion of the venous access line 130 proximate the venous needle assembly 134. The clamp 138f is positioned to engage the fluid line 137 of the venous needle assembly 134. The clamp 138g is positioned to engage the fluid line 114. The clamps 138a-138g can be independently actuated to control fluid flows through the arterial line set 104, the venous line set 108, and the fluid line 114.

A fluid flow sensor 140a is positioned to detect fluid flow through the arterial drip chamber 124, and a fluid flow sensor 140b is positioned to detect fluid flow through the venous drip chamber 132. The fluid flow sensors 140a, 140b can, for example, be optical sensors responsive to drops of fluid through the arterial drip chamber 124 and the venous drip chamber 132, respectively. The fluid flow sensors 140a, 140b can detect flow rates of fluid flowing through the arterial drip chamber 124 and the venous drip chamber 132, respectively. In addition, the fluid flow sensors 140a, 140b can distinguish between fluids having different opacities, such as blood and saline. For example, during operation of the blood pump 118, the type of fluid flowing through the arterial drip chamber 124 and the venous drip chamber 132 may vary depending on the stage of the extracorporeal treatment. The fluid flow sensors 140a, 140b can, for example, distinguish between the different types of fluid and provide the controller 144 with a signal indicative of a current stage of the extracorporeal treatment process.

Whereas the arterial line set 104, the dialyzer 110, and the venous line set 108 form the extracorporeal blood circuit, the hemodialysis machine 106 includes components that form a dialysis fluid circuit with the dialyzer 110. The dialysate lines and other components that form the dialysis fluid circuit are located inside the hemodialysis machine 106 and thus are not visible in FIG. 1. The extracorporeal blood circuit and the dialysis fluid circuit extend alongside one another through the dialyzer 110 such that the blood and the dialysis fluid flow adjacent one another through the dialyzer 110 during an extracorporeal treatment. Flow of the blood and the dialysis fluid through the dialyzer 110 filters the blood by causing waste substances from the blood to diffuse into the dialysis fluid.

The hemodialysis machine 106 also includes an ultrafiltration pump 142 (shown in FIG. 1A) to draw liquid, e.g., water, from the blood circulating through the dialyzer 110. The ultrafiltration pump 142 generates a pressure on the dialysis fluid circuit, thereby creating a pressure differential between the dialysis fluid circuit and the extracorporeal blood circuit. This pressure differential can cause liquid, e.g., water, to be withdrawn from the blood of the patient 160 through the dialyzer 110. During the ultrafiltration process, water is drawn from the extracorporeal blood circuit, through the dialyzer 110, and into a waste line of the dialysis fluid circuit.

The hemodialysis machine 106 also includes a dialysis fluid pump 143 (shown in FIG. 1A) operably connected to the dialysis fluid circuit. During an extracorporeal treatment, the dialysis fluid pump 143 is operated to circulate the dialysis fluid through the dialysis fluid circuit. The dialysis fluid pump 143 draws dialysis fluid from a dialysis fluid source, through the dialyzer 110, and then into a dialysis fluid drain.

The hemodialysis machine 106 further includes a controller 144 (shown in FIG. 1A) operably connected to the blood pump 118, the pressure transducers 125a, 125b, the fluid flow sensors 140a, 140b, the ultrafiltration pump 142, the dialysis fluid pump 143, the user interface system 150, and various alert devices 1006, 1008, 1012 (described further below). The controller 144 automatically controls operations of the blood pump 118 during the extracorporeal treatment. The controller 144 operates the blood pump 118 based on flow rates detected by one or more of the fluid flow sensors 140a, 140b. Alternatively or additionally, the controller 144 operates the blood pump 118 based on pressures detected by one or more of the pressure transducers 125a, 125b.

The user interface system 150 is operable by the operator to monitor and control operations of the hemodialysis machine 106. The user interface system 150 includes a touchscreen 151 and a display 152. The operator can manually operate the touchscreen 151 to control operations of the hemodialysis machine 106, and the display 152 can provide visual indications to the operator. The user interface system 150 is integral to the hemodialysis machine 106 in the embodiment shown in FIG. 1A.

A method of using the hemodialysis system to carry out a dialysis treatment will now be described. To prepare for a treatment, the hemodialysis machine 106 is first powered on. The hemodialysis machine 106 may either be powered on manually by the user or powered on automatically.

Upon powering on the hemodialysis machine 106, a number of integrity tests are automatically performed. These integrity tests include a battery test to confirm functionality of the battery of the hemodialysis machine 106 should power be interrupted during treatment. The integrity tests also include a dialysate conductivity test to ensure that the prepared dialysate includes a proper concentration of electrolytes and salts for performing the hemodialysis treatment. The integrity tests also include a check that ensures the readings from an internal independent conductivity cell match readings from a primary conductivity cell. The integrity tests also include a dialysate temperature test to check that the dialysate is being held at a proper temperature for performing the hemodialysis treatment. These integrity tests are performed automatically upon powering on the hemodialysis machine 106. The blood line set need not be attached to the hemodialysis machine for the integrity tests to be performed.

After powering on the hemodialysis machine 106, the user interface system 150 displays a series of set up screens that help the user to set up the hemodialysis machine for treatment. The set-up screens can, for example, explain how to connect the various lines and components of the blood line set to the hemodialysis machine 106.

Once the blood line set has been properly connected to the hemodialysis machine 106, as shown in FIG. 1A, the user interface system 150 displays screens to walk the user through a priming process that is carried out to remove air from the blood line set.

Figure 2:
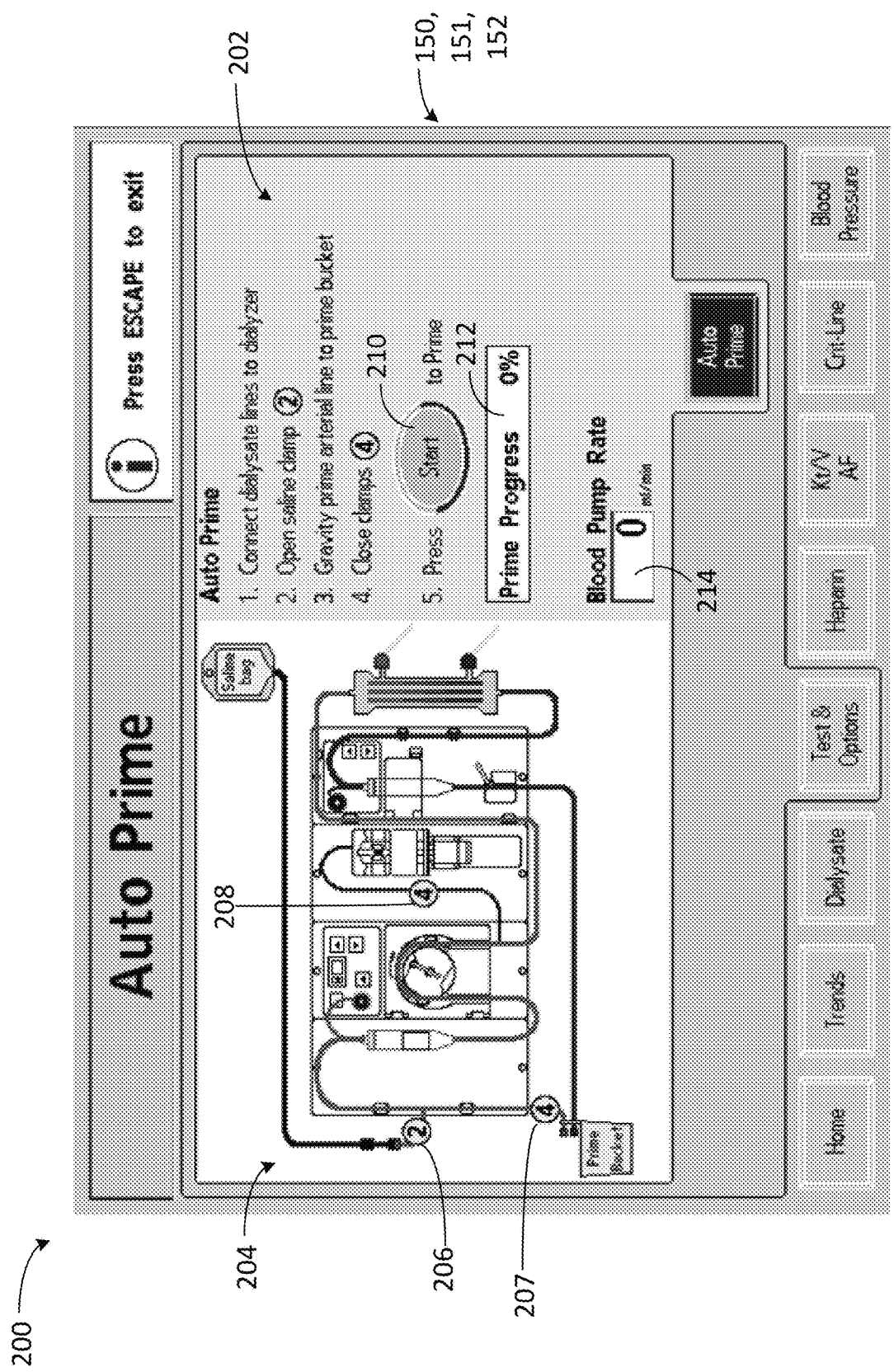
FIG. 2 is a schematic of an automatic priming interface with instructions for setting up an automatic priming procedure for the hemodialysis system of FIGS. 1A and 1B.

The automatic priming interface 200 shown in FIG. 2 is an example of a screen that can be displayed by the user interface system 150 to assist the user with priming. As shown, the automatic priming interface 200 includes a first set of instructions 202 for performing a first portion of the automatic priming procedure and a graphical representation 204 of the hemodialysis machine 106. The graphical representation 204 includes numeric labels 206-208 corresponding to hemodialysis machine components described in the set of instructions 202. The set of instructions 202 includes five steps. The first step instructs a user to connect the dialysate lines to the dialyzer. After reading this first step, the user connects the dialysate lines to the dialyzer. The second step instructs the user to open a saline clamp indicated by the numeric label 206 to allow a saline solution to flow from the saline bag, through the saline supply line 114 and then through the arterial line set 104. After reading this second step, the user opens the saline clamp indicated by numeric label 206. This step primes the saline supply line 114 and the arterial line set 104 using gravity to move the saline, indicated by the third step of the instructions 202. Upon completing the gravity prime of the saline supply line 114 and the arterial line set 104, the user is instructed, in step four, to close clamps indicated by the numeric labels 207 and 208, which closes the arterial line set 104. The user closes the clamps indicated by the numeric labels 207 and 208 to close the arterial line set 104. With the arterial line set 104 closed, when the blood pump 118 is run, saline is pulled from the saline bag 112 through the supply line 114 and the arterial line set 104 through the blood pump 118 and to the dialyzer 110. After running through the dialyzer 110, the solution is pumped through the venous line set 108 to the waste container 168.

To begin the automated portion of the pumping process, the user presses the start button 210 as indicated in the fifth instruction of the instruction set 202. A progress bar 212 indicates the completeness of the first portion of the automatic priming procedure as the saline solution is pumped through the hemodialysis machine 106. A blood pump rate indicator 214 displays the pumping rate of the blood pump 118. When a particular volume of saline has been pumped, or a particular pumping time has been reached, the progress bar 212 will show that the first portion of the automatic priming procedure is complete. Upon completing the first portion of the automatic priming procedure, the automatic priming interface will display a second set of instructions for a recirculation portion of the automatic priming procedure, as shown in FIG. 3.

Figure 3:
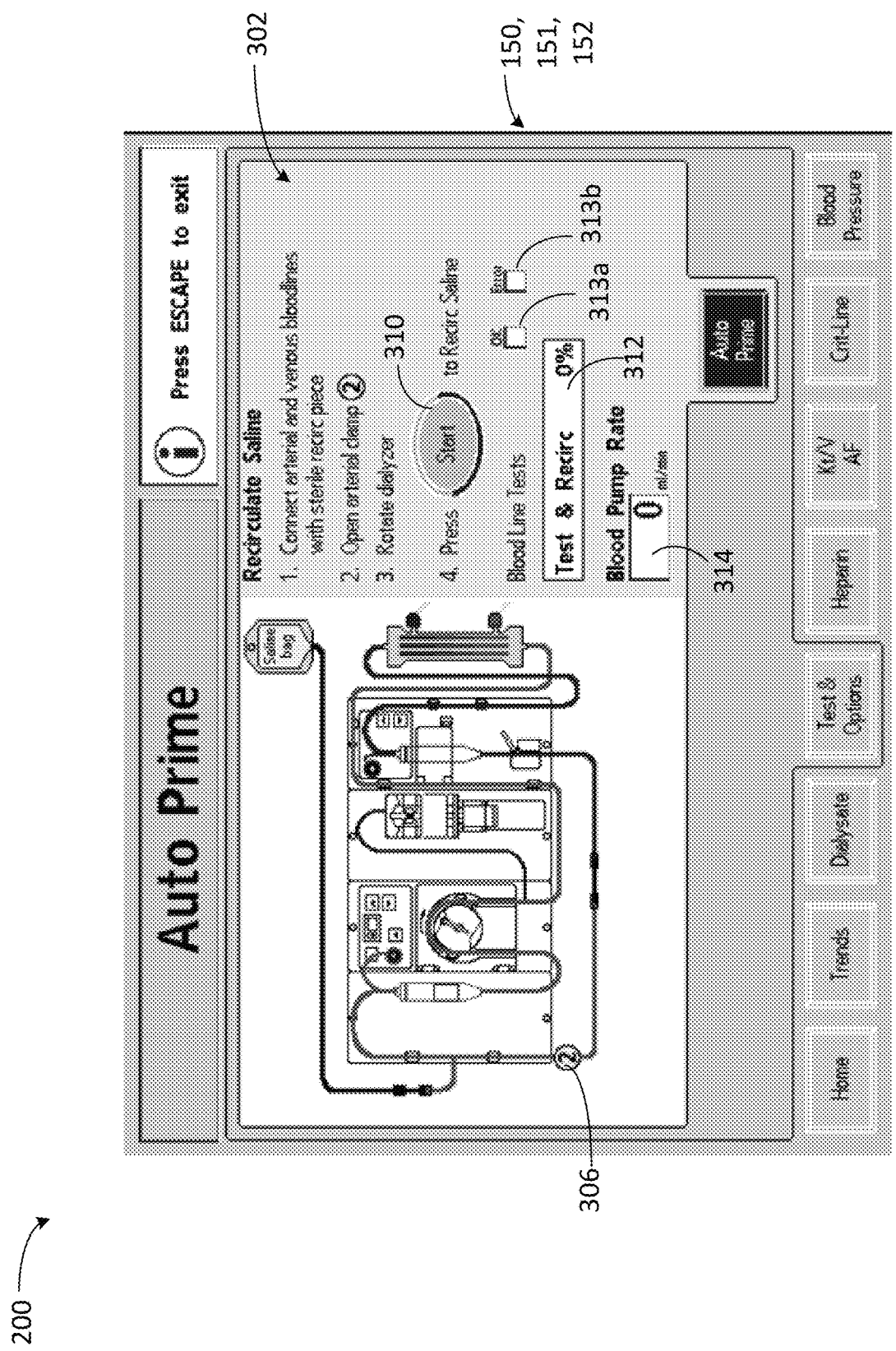
FIG. 3 is a schematic of an automatic priming interface with instructions for recirculating a priming fluid in an extracorporeal blood circuit of the hemodialysis system of FIGS. 1A and 1B.

Referring to FIG. 3, the automatic priming interface 200 displays a second set of instructions 302 and a second graphical representation 304 of the hemodialysis machine 106. FIG. 3 is a schematic of an automatic priming interface with instructions for recirculating a priming fluid in the bloodline circuit. The second graphical representation 304 includes a numeric label 306 corresponding to a hemodialysis machine component described in the second set of instructions 302. The second set of instructions 302 includes four steps. The first step instructs the user to connect the arterial line set 104 and the venous line set 108 together with a sterile recirculation piece. After reading this first step of the instructions, the user connects arterial line set 104 to the venous line set 108 with the sterile recirculation piece. The second step instructs the user to open an arterial clamp represented by numerical label 306. The user opens the clamp represented by numerical label 306. When the arterial line set 104 and the venous line set 108 are connected in such a way and the clamp represented by numerical label 306 is opened, instead of the saline flowing to the waste container 168, the saline is recirculated from the venous line set 108 into the arterial line set 104. The third step instructs the user to rotate the dialyzer 110. After reading this third step of the instructions, the user rotates the dialyzer. Rotating the dialyzer 110 allows air trapped in the dialyzer 110 to be released as the saline flows through the dialyzer 110 in the recirculation portion of the automatic priming procedure.

To begin the recirculation procedure, the user presses the start button 310 as indicated in the fourth instruction of the instruction set 302, which starts the blood pump 118. A progress bar 312 displays the progress of the recirculation procedure and the functionality tests that are automatically performed during recirculation. Check boxes 313a and 313b display whether the tests have indicated errors in the functionality of the hemodialysis machine 106. A blood pump rate indicator 314 displays the pumping rate of the blood pump 118 during recirculation. When a particular volume of saline has been pumped, a particular pumping time has been reached, and/or the functionality tests have been completed, the progress bar 312 will show that the recirculation portion of the automatic priming procedure is complete. Upon completing the recirculation portion of the automatic priming procedure, the automatic priming interface 200 is removed from the display 152 of the hemodialysis machine 106 and a hemodialysis treatment interface is displayed to indicate that the hemodialysis machine 106 is ready for treatment.

The functionality tests performed during recirculation include a positive pressure test and a negative pressure test. In the positive and negative pressure tests, the dialysis machine checks that a dialysate pressure of at least a certain positive level and a certain negative level, respectively, can be achieved. If either test fails, an operator or a service technician may check the hydraulics of the dialysis machine for leaks or faulty sensors. The functionality tests also include an optical detector test. In the optical detector test, an optical detector is used to check for air bubbles in the circulating saline solution.

The functionality tests also include a transmembrane pressure test, which calculates the transmembrane pressure across a semi-permeable membrane of the dialyzer 110 and compares the calculated transmembrane pressure to an acceptable operating range of transmembrane pressures. An error is returned if the transmembrane pressure is outside of the acceptable operating range. An error in the transmembrane pressure test may indicate that the dialyzer 110 has not been properly connected to the hemodialysis machine 106 or that the dialyzer 110 is defective and should not be used in hemodialysis treatment.

The functionality tests also include a venous pressure test and an arterial pressure test. During the venous pressure test, a pressure is measured by pressure transducer 125b and compared to an acceptable operating range. An error is returned if the venous pressure is outside of the acceptable operating range. During the arterial pressure test, a pressure is measured by pressure transducer 125a and compared to an acceptable operating range. An error is returned if the arterial pressure is outside of the acceptable operating range. Based on the value of the pressures measured by pressure transducers 125a and 125b, the hemodialysis machine 106 may determine that one or more components of the hemodialysis machine 106 are improperly connected.

Figure 4:
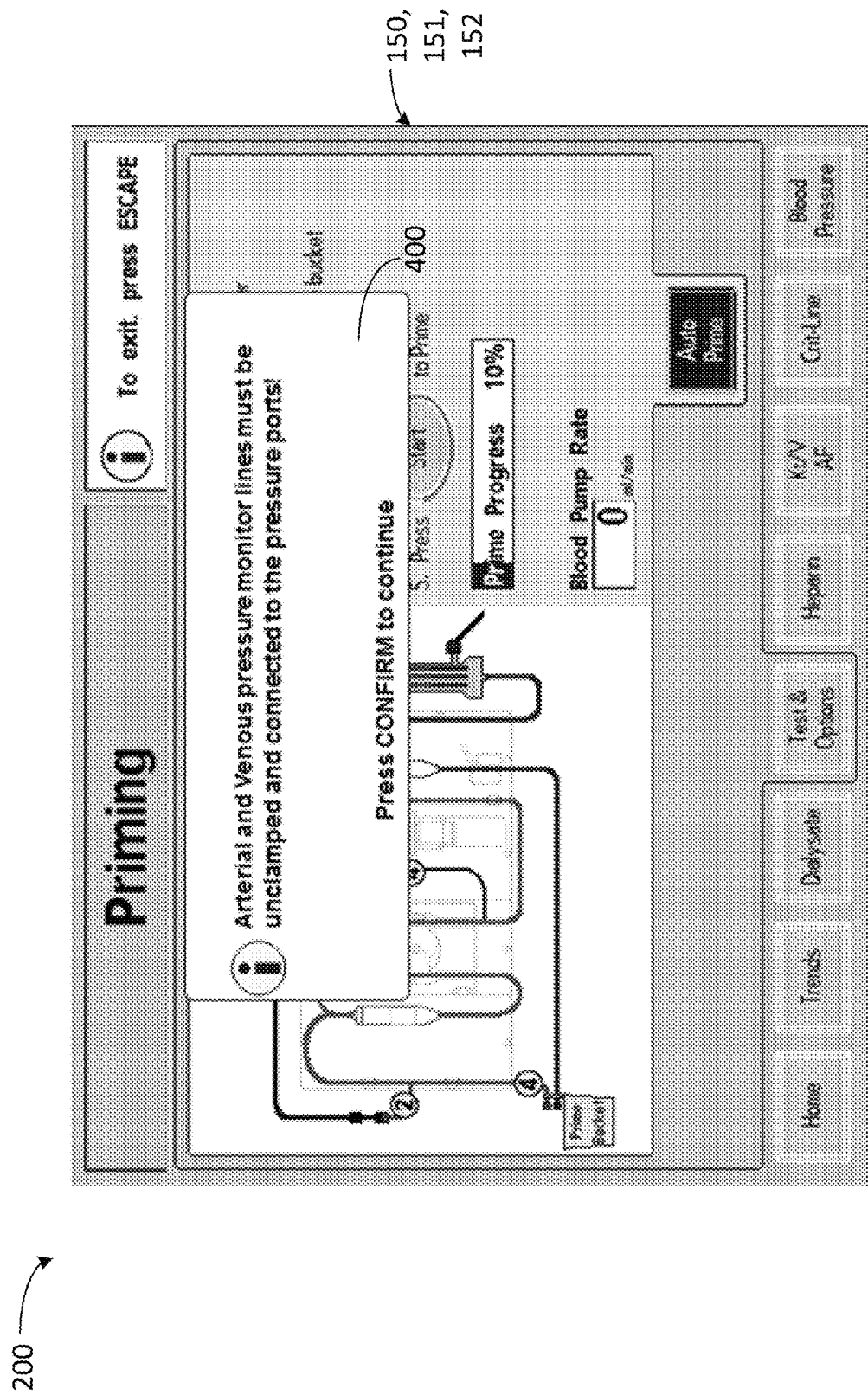
FIGS. 4-6 are schematics of error messages that may arise during priming.
Figure 5:
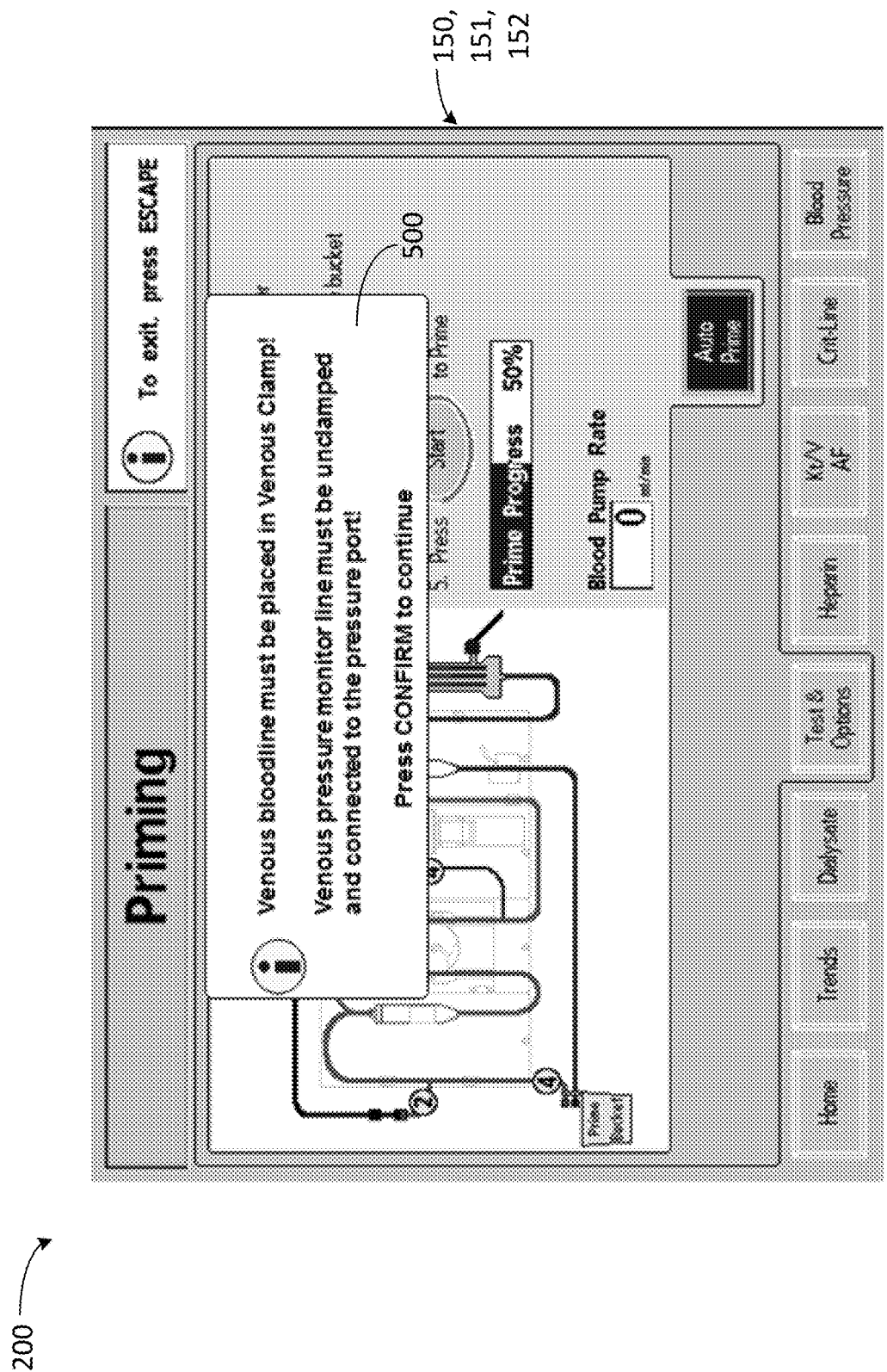
Figure 6:
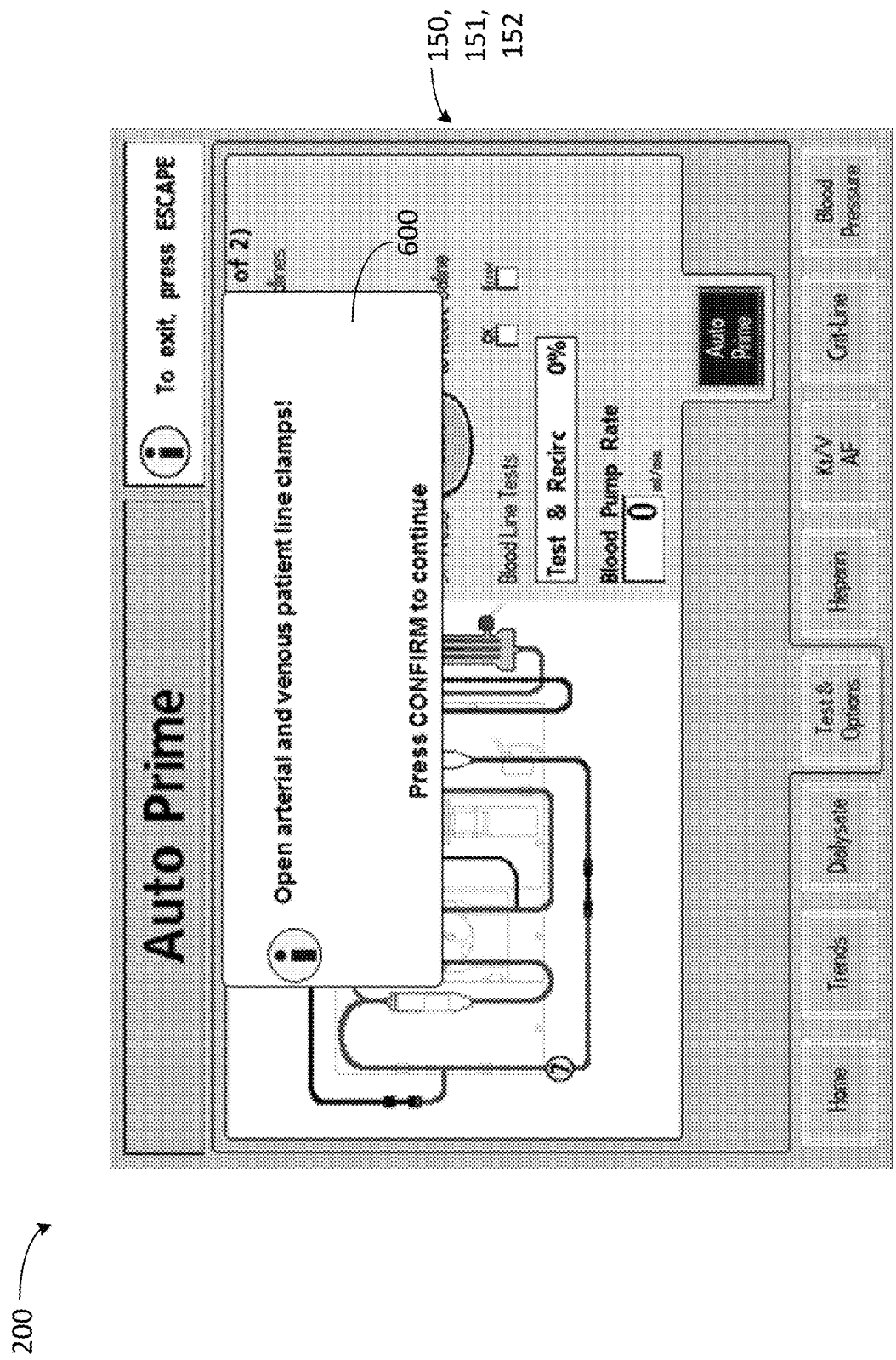

Referring to FIG. 4, based on the results of the arterial and venous pressure tests, the hemodialysis machine 106 determined that the arterial and venous lines were either clamped and/or not connected to the pressure ports and returned error message 400 to the user. Referring to FIG. 5, based on the results of the venous pressure test, the hemodialysis machine 106 determined that the venous line set 108 was not placed in the venous clamp and that the venous pressure monitor line 131 must be unclamped and connected to the pressure port. As such, the hemodialysis machine 106 returned error message 500 to the user. Referring to FIG. 6, based on the results of the arterial and venous pressure tests, the hemodialysis machine 106 determined that the arterial and venous line clamps were not opened. As such, the hemodialysis machine 106 returned error message 600 to the user.

The functionality tests also include a blood leak detection test. If a leak is found at a blood detector, the controller 144 sends a control signal to close a clamp and turn off the blood pump 118 to prevent further blood leakage. To correct a blood test failure, an operator ensures that there are no air bubbles in the dialysate lines.

The functionality tests also include a level detection test. The level detection test checks, with an optical detector, the level in the venous drip chamber 132. The optical detector communicates with the controller 144 of the hemodialysis machine 106 and the controller, if the level is too high or too low, sends a control signal to correct the level in the venous drip chamber 132. In some instances, the controller closes a clamp, turns off the blood pump 118, and sounds a level detector alarm. In some instances, the level detector includes ultrasonic heads configured to send an ultrasonic signal across the level detector. To correct a test failure, an operator ensures that the venous drip chamber 132 is properly positioned in a holder. If the level detector incudes ultrasonic heads, the operator ensures that the ultrasonic heads are clean.

Each of the tests may raise one or more alarms on the hemodialysis machine 106 if the result of the test is outside of an expected parameter range. The hemodialysis machine 106 is configured to troubleshoot when a test result is outside of the expected parameter range and provide specific alarms to a user. The specific alarms, examples of which are shown in FIGS. 4-6, guide the user to fix a problem causing the alarm by indicating which component of the hemodialysis machine 106 must be addressed. For example, the various pressure sensing functionality tests (e.g., the venous pressure test, the arterial pressure test, etc.) are sensitive enough to detect minor clamps being properly closed (e.g., a heparin clamp, a clamp to a medication port).

An example of an extracorporeal treatment will now be described with respect to FIG. 1B. FIG. 1B illustrates a portion of the hemodialysis system 100 when the patient 160 is undergoing an extracorporeal treatment. Before the extracorporeal treatment is initiated, a human operator, e.g., a clinician, a nurse, or other clinical personnel, positions the arterial line set 104, the venous line set 108, the fluid line 114, and the saline bag 112 in preparation for the extracorporeal treatment. The operator positions the arterial line set 104 such that the blood pump 118 engages a portion of the arterial line 122 and connects the fluid line 114 to the port 139 of the arterial line set 104 using the connectors 141e, 141f. The operator also mounts the arterial drip chamber 124 and the venous drip chamber 132 adjacent the fluid flow sensors 140a, 140b to enable the fluid flow sensors 140a, 140b to detect fluid flow through the arterial drip chamber 124 and the venous drip chamber 132, respectively. The operator mounts the dialyzer 110 to the hemodialysis machine 106 and connects the arterial line 122 and the venous line 128 to the dialyzer 110.

The operator then places the arterial line set 104 and the venous line set 108 in fluid communication with the circulatory system of the patient 160. The operator connects the fluid line 129 of the arterial needle assembly 126 to the arterial access line 120 using the manually operable connectors 141a, 141b. The operator also connects the fluid line 137 of the venous needle assembly 134 to the venous access line 130 using the manually operable connectors 141c, 141d. The operator further inserts the arterial needle assembly 126 (connected to the arterial access line 120) into an arterial access 146 of the patient 160, and inserts the venous needle assembly 134 (connected to the venous access line 130) into a venous access 148 of the patient 160. The arterial needle assembly 126, the arterial line set 104, the venous line set 108, the venous needle assembly 134, and the dialyzer 110 thus form an extracorporeal circuit connected to the circulatory system of the patient 160. For example, the arterial line set 104 and the venous line set 108 are in fluid communication with one another through the dialyzer 110 and are both in fluid communication with the circulatory system of the patient 160.

The operator also connects the fluid line 114 to the port 139 of the arterial line set 104 using the manually operable connectors 141e, 141f. This places the saline bag 112 in fluid communication with the arterial line set 104 and hence the extracorporeal circuit. For example, the fluid line 114 is connected in parallel with the arterial access line 120 such that negative pressure generated along the arterial line 122 draws blood from the patient 160 as well as fluid through the fluid line 114 into the arterial line 122. The operator positions the fluid line 129 of the arterial needle assembly 126 to enable the clamp 138a to be engaged with the fluid line 129. The arterial line set 104 is positioned to enable the clamp 138b to be engaged with the fluid line 129 of the arterial needle assembly 126. The arterial line set 104 is also positioned to enable the clamp 138c to be engaged with the port 139.

The operator positions the venous line set 108 to enable the clamp 138d to be engaged with an outlet of the venous access line 130 extending from the venous drip chamber 132. The venous line set 108 is also positioned to enable the clamp 138e to be engaged with a portion of the venous access line 130 between the outlet from the venous drip chamber 132 and the fluid line 137 of the venous needle assembly 134. The venous needle assembly 134 is positioned to enable the clamp 138f to be engaged with the fluid line 137 of the venous needle assembly 134. The operator positions the fluid line 114 to enable the clamp 138g to be engaged with the fluid line 114.

By positioning these portions of the arterial line set 104, the venous line set 108, and the fluid line 114 in this manner, fluid flow through each of the fluid line 114, the arterial needle assembly 126, the arterial line set 104, the venous needle assembly 134, and the venous line set 108 can be independently controllable through operation of the clamps 138a-138g. In preparation for the extracorporeal treatment, each of the clamps 138a-138g are placed in open positions such that flow is allowed through each of the arterial needle assembly 126, the arterial line set 104, the venous line set 108, the venous needle assembly 134, and the fluid line 114.

The operator connects a dialysis fluid source to the dialysis fluid circuit to enable dialysis fluid to be circulated through the dialyzer 110. The operator also connects a drain line to the dialysis fluid circuit so that spent dialysis fluid, e.g., dialysis fluid that has flown through the dialyzer 110 and that has received waste substances from the blood, can be discarded into a drain through the drain line. The drain line can further receive ultrafiltrate drawn from the blood during the ultrafiltration process facilitated by operation of the ultrafiltration pump 142.

After the operator has set up the arterial line set 104, the venous line set 108, and the fluid line 114 and has set up the dialysis fluid circuit, the operator initiates the extracorporeal treatment, thereby triggering automated control of the extracorporeal treatment by the controller 144. During the extracorporeal treatment, the blood pump 118 is operated to circulate blood through the dialyzer 110. The controller 144 can control the blood pump 118 through feedback control based on pressures detected by the pressure transducers 125a, 125b or based on flow rates detected by the fluid flow sensors 140a, 140b. The blood pump 118 is driven such that blood in the arterial line set 104 is drawn from the patient 160 and directed toward the dialyzer 110 and the venous line set 108. For example, the blood pump 118 generates a negative pressure along the portion of the arterial line set 104 between the patient 160 and the blood pump 118 and a positive pressure along the portion of the arterial line set 104 between the blood pump 118 and 30 the dialyzer 110 and along the venous line set 108. If the blood pump 118 is a peristaltic pump, the blood pump 118 is rotated in a rotational direction 145, thereby generating this pressure differential to circulate blood through the extracorporeal blood circuit.

The dialysis fluid pump 143 is operated to circulate dialysis fluid through the dialyzer 110. Waste substances from the blood diffuse into the dialysis fluid. In addition, the ultrafiltration pump 142 is operated to draw excess fluid from the extracorporeal blood circuit into the dialysis fluid circuit.

Figure 7:
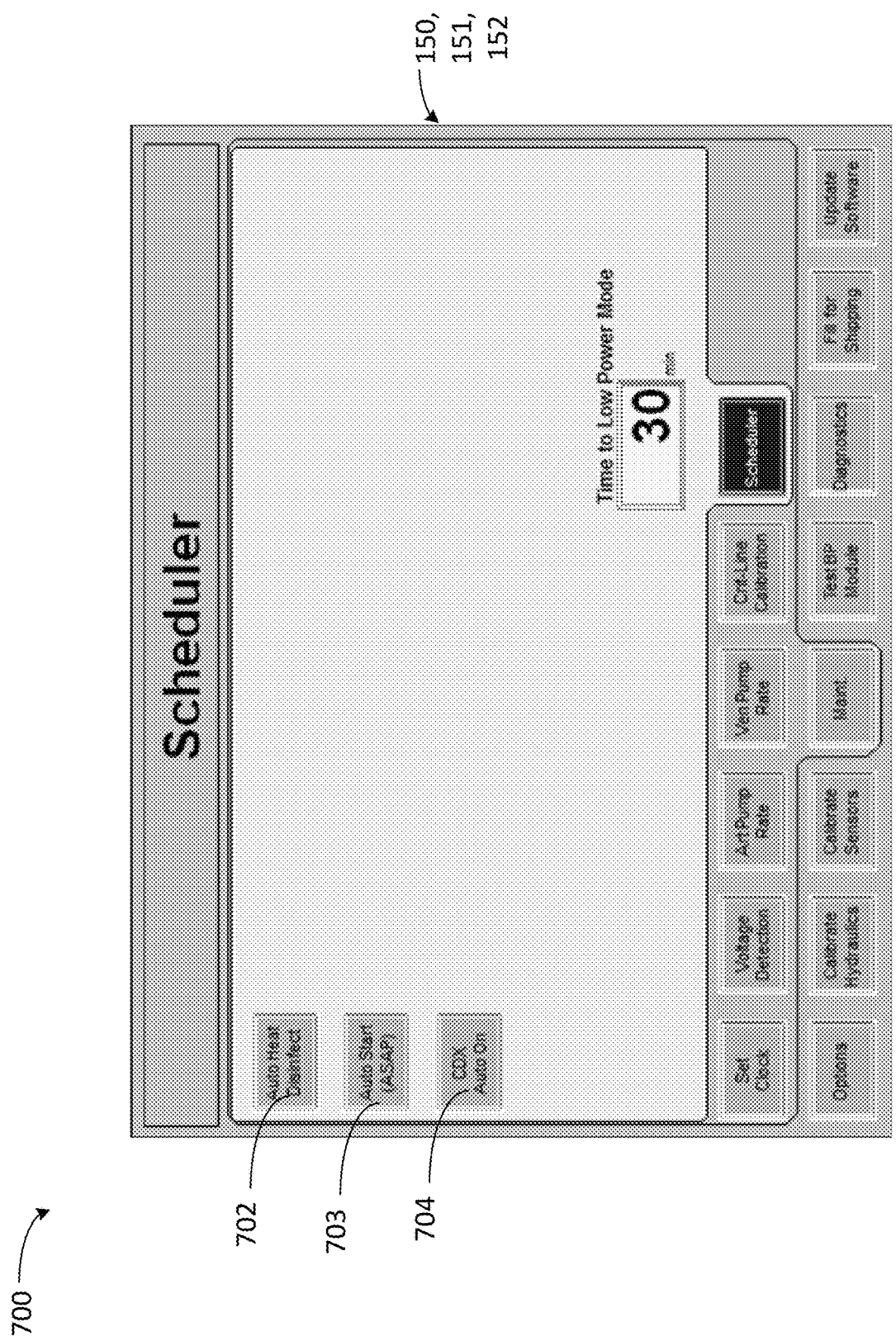
FIG. 7 is a schematic of a scheduling interface of the hemodialysis system of FIGS. 1A and 1B.

While the method described above involved the user manually powering on the hemodialysis machine 106, in certain implementations, the hemodialysis machine 106 can be programmed to automatically power on at a desired time. Likewise, the hemodialysis machine 106 can be programmed to carry out various other automated functions. For example, FIG. 7 shows a schematic of a scheduling interface 700 that allows a user to select a particular task to be scheduled. Scheduled tasks are represented by buttons 702-704 and include turning on the hemodialysis machine 106, beginning testing, or running a decontamination protocol. The scheduling interface 700 also includes a low power mode indicator 706, which indicates an amount of time during which the hemodialysis machine 106 will remain turned on after a user interaction before switching to a low power mode if no subsequent user interactions occur.

By pressing one of the buttons 702-704, the user is brought to a screen to select parameters for the task to be scheduled. Examples of screens for turning on the hemodialysis machine 106, beginning testing, or to running a decontamination protocol are shown in FIGS. 8-10, respectively.

Figure 8:
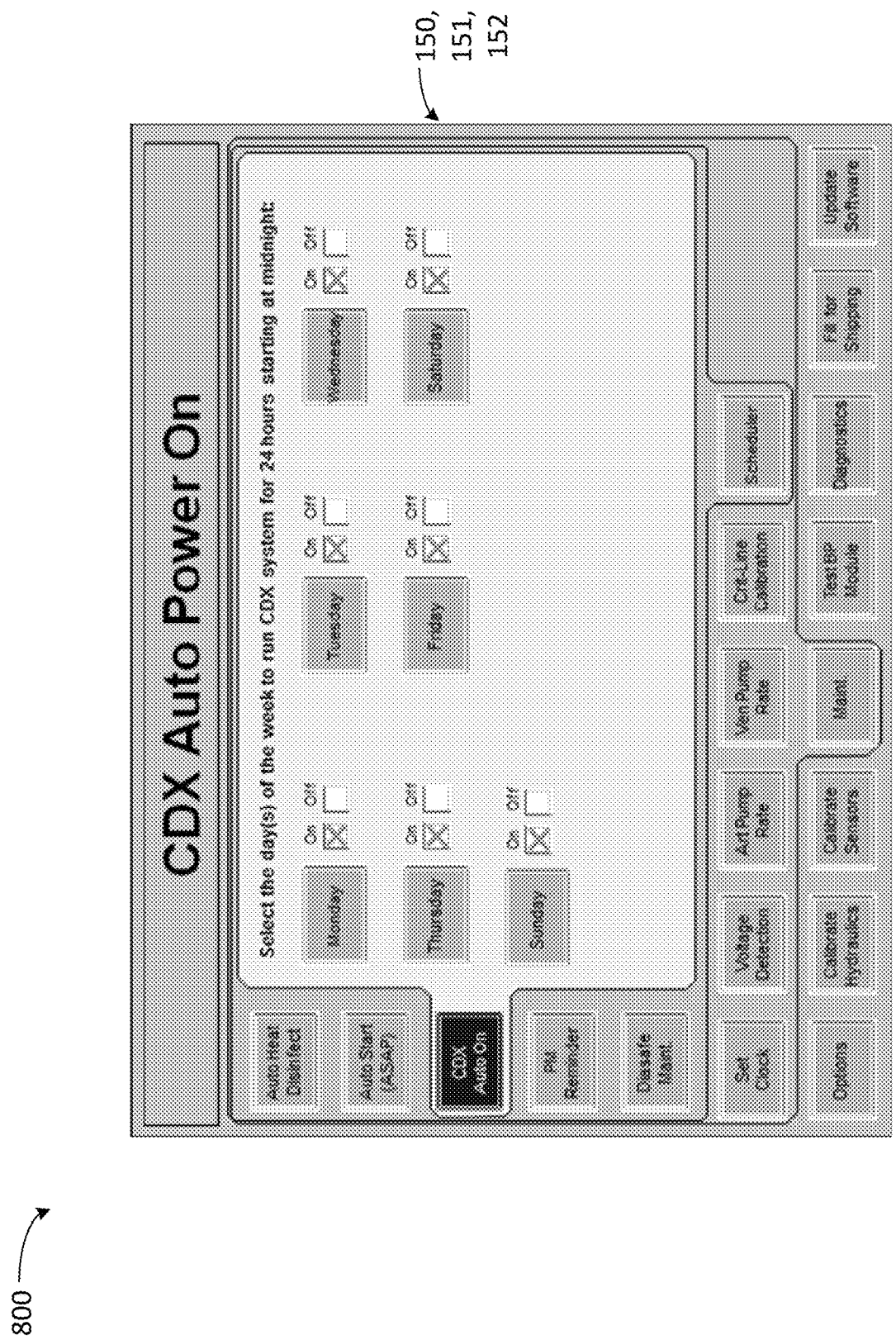
FIG. 8 is a schematic of a scheduling interface for an automatic power on feature for the hemodialysis system of FIGS. 1A and 1B.

Referring to FIG. 8, a screen 800 is displayed that presents the days of the week, Monday through Sunday, and two check boxes for each day, one labeled 'On' and the other labeled 'Off'. The user may check the 'On' checkbox next to a day of the week to have the hemodialysis machine 106 turn on at midnight and operate for 24 hours on the corresponding day of the week. Any number of 'On' checkboxes may be selected and may correspond to days where a dialysis clinic in which the hemodialysis machine 106 is located is open and/or treating patients.

While the screen 800 indicates that the hemodialysis machine 106 can be turned on at midnight, it should be understood that the hemodialysis machine 106 could be programmed to automatically turn on at any of various other desired times.

Figure 9:
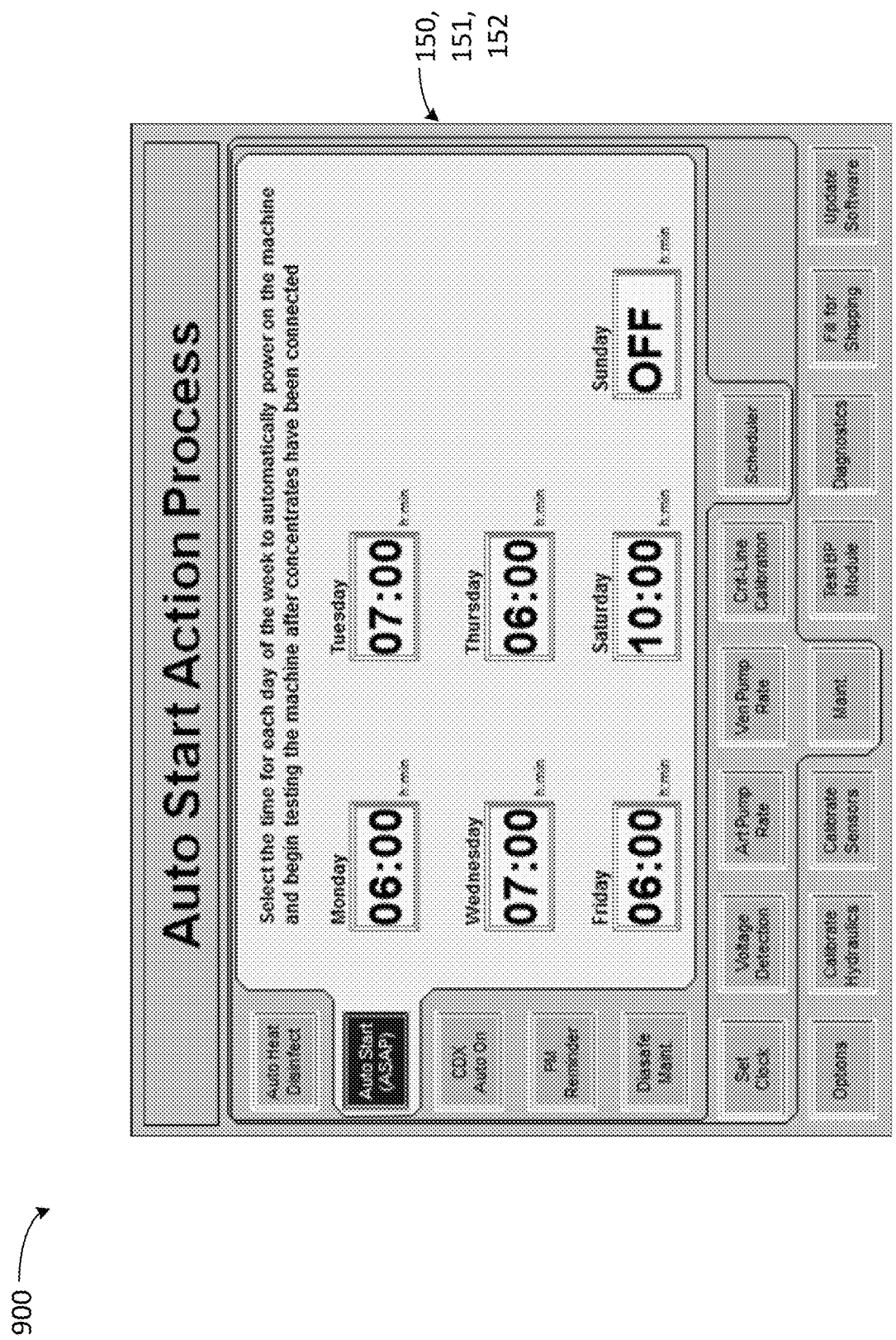
FIG. 9 is a schematic of a scheduling interface for an automatic power on and test feature for the hemodialysis system of FIGS. 1A and 1B.
Figure 10:
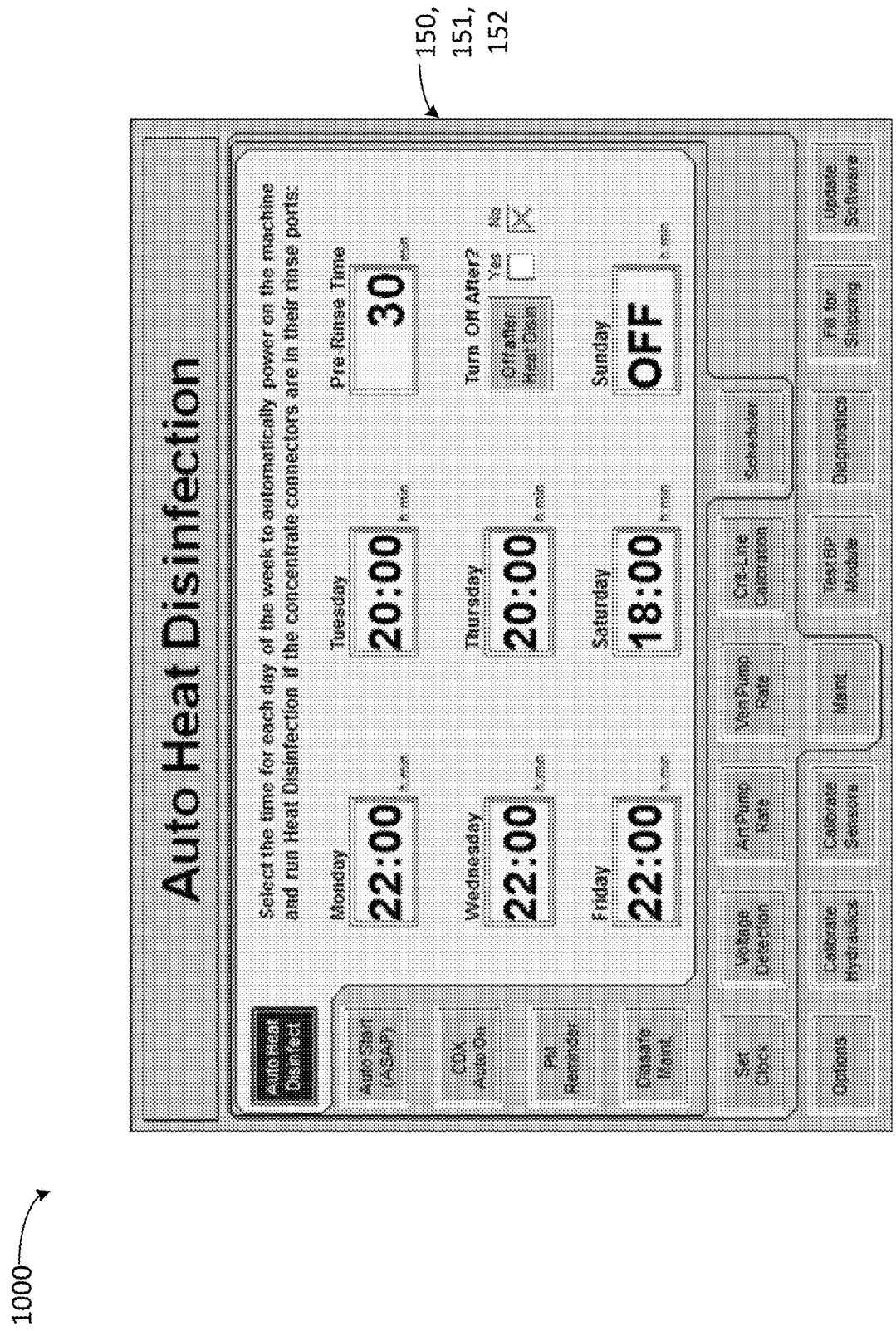
FIG. 10 is a schematic of a scheduling interface for an automatic heat disinfection feature for the hemodialysis system of FIGS. 1A and 1B.

Referring to FIG. 9, a screen 900 is displayed that presents the days of the week, Monday through Sunday, and a selectable time corresponding to each day of the week. The selectable time may be set to any time at which the user desires the hemodialysis machine 106 to automatically power on and begin integrity tests, as described above, after concentrates, for creating the dialysate, have been connected. The selectable time may also be set to 'OFF' if the user does not desire the hemodialysis machine to automatically power on and begin integrity tests on that day of the week. For example, using this scheduler, the concentrates may be connected at the end of a treatment day and a time for automatic power on and integrity testing may be selected for the next treatment day before the dialysis clinic in which the hemodialysis machine 106 is located opens. The hemodialysis machine 106 is ready for the user to begin the priming procedure as the user's first interaction with the hemodialysis machine 106 for that day.

In some cases, a clinic may have one clinician arrive to the clinic early to connect all necessary concentrates to the machines in the clinic so those machines are equipped to perform priming procedures and dialysate making procedures upon automatic startup.

Referring to FIG. 10, a screen 1000 is displayed that presents the days of the week, Monday through Sunday, and a selectable time corresponding to each day of the week. The selectable time may be set to any time at which the user desires the hemodialysis machine 106 to automatically power on and perform a disinfection procedure. The selectable time may also be set to 'OFF' if the user does not desire the hemodialysis machine 106 to automatically perform the disinfection procedure on that day of the week. To perform the disinfection procedure, the concentrate connectors must be connected to rinse ports so the concentrates are not contaminated during the disinfection protocol and so that the disinfection solution (e.g., hot water) may be introduced into the hemodialysis machine 106. The screen 1000 also includes a selectable pre-rinse time and an option to select whether the hemodialysis machine 106 should be turned off or remain on after the disinfection protocol is complete.

For example, the concentrate connectors may be connected to the rinse ports at the end of a treatment day and a time for automatic disinfection may be selected for a time during the night when the dialysis clinic is closed. The disinfection protocol is run during the night which is more efficient because the disinfection protocol would not have to be run during treatment hours at the dialysis clinic when the hemodialysis machine could be performing hemodialysis treatment. If the hemodialysis machine is selected to remain on after the disinfection protocol, the user would switch the connectivity of the concentrate connectors, at which time automatic integrity tests may begin according to the previously mentioned protocol in FIG. 9.

Referring again to FIG. 1A, for example, the hemodialysis machine 106 is configured to notify the operator or technician that the hemodialysis machine 106 is powering on using an auditory alert 1006, such as a siren. When the hemodialysis machine 106 begins to power on, the siren will emit a sound to notify a person in the area that the hemodialysis machine 106 is powering on. This may be particularly useful when performing maintenance on the hemodialysis machine 106, as the technician may not know the normal operating schedule of the hemodialysis machine 106. Thus, the technician may be working on internal components of the hemodialysis machine 106 when the hemodialysis machine 106 is programmed to automatically turn on. The alert 1006 notifies the operator or technician who is then able to clear the area and/or remove tools or hands from the hemodialysis machine 106 prior to the hemodialysis machine 106 moving components, such as pumps and clamps, and/or prior to a high voltage being applied to certain parts of the hemodialysis machine.

As an alternative to or in addition to being configured to emit an auditory alert, the hemodialysis machine 106 may be configured to visually notify an operator that the hemodialysis machine 106 is powering on. FIG. 1 shows a visual alert 1008 using one or more lights located at the top of the hemodialysis machine 106. Alternatively or additionally, a visual alert 1010 may be displayed on the user interface of the hemodialysis machine 106. The visual alert 1008 may emit a solid constant signal or may blink to further attract attention of a user. The color of the visual alert 1008 may be red or a combination of colored LEDs to produce a color unique to the powering on visual alert 1008. For example, if the hemodialysis machine 106 commonly uses red to signify an alert or warning during use of the hemodialysis machine 106, the powering on visual alert 1008 may emit a green light. Similarly, a unique blinking pattern may be used to indicate the hemodialysis machine 1002 is turning on.

Still referring to FIG. 1, the hemodialysis machine 106 may also be configured to vibrate when powering on. The vibrational alert 1012 notifies technicians and people surrounding the hemodialysis machine 106 that the hemodialysis machine 106 is powering on. The vibrational alarm 1012 is particularly useful when a technician is working on internal components within the hemodialysis machine 106. The vibrational alert 1012 quickly indicates to the technician that the hemodialysis machine 106 is self-powering on. An added benefit is that the vibration alert 1012 does not disrupt or add to the noise of the clinic if the hemodialysis machine 106 is turned on during operating hours. The vibrational alert 1012 may produce a constant signal or a patterned signal, such as an alternating vibration strength. In some cases, for example, the device strongly vibrates for 2 seconds and softly vibrates for 1 second, in order to draw the attention of the technician.

The above-described alerts may be combined in any manner to create an alert system that is most appropriate for the particular setting in which the hemodialysis machine is being used.

Figure 11:
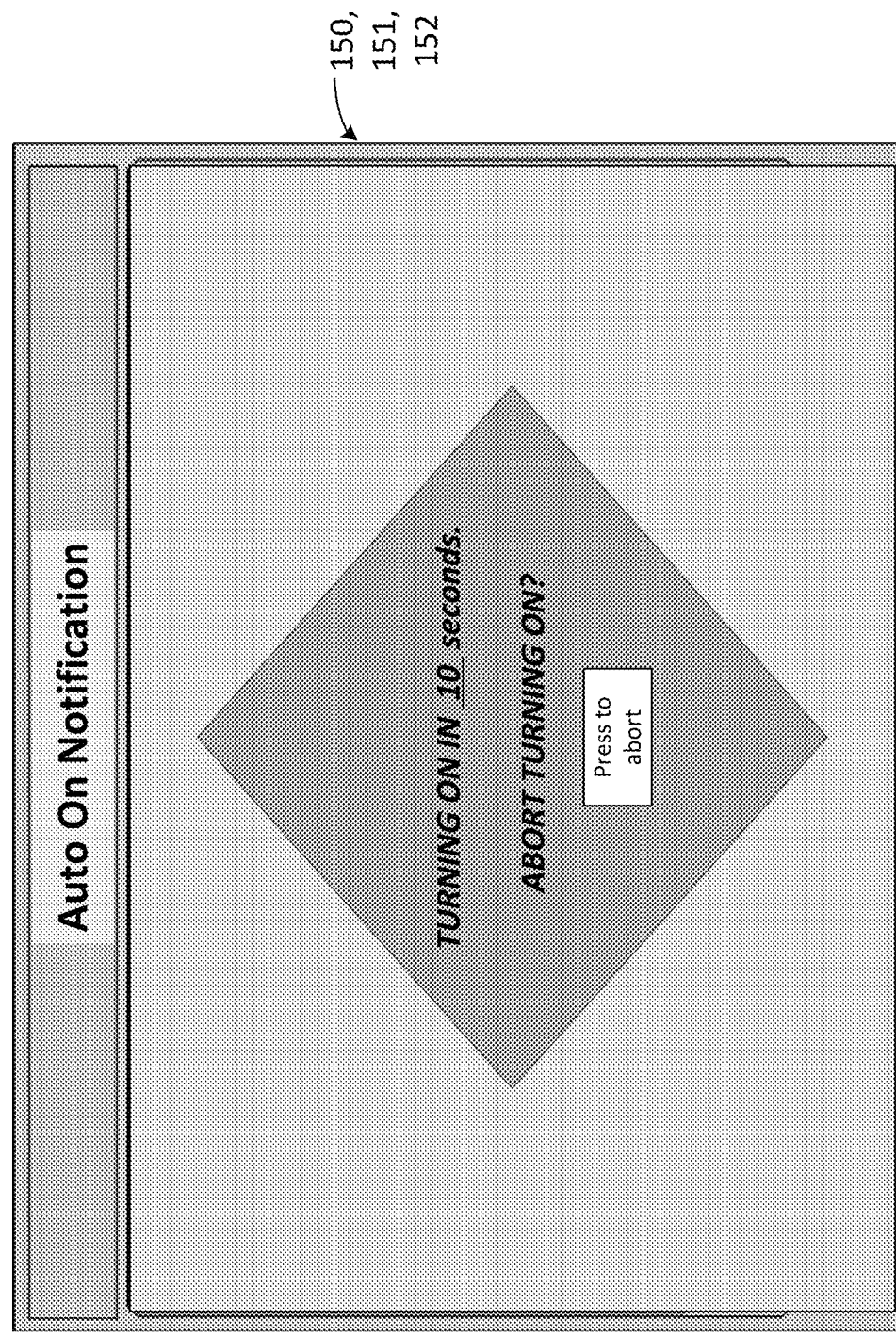
FIG. 11 is a schematic of an alert interface for alerting the operator of the hemodialysis system of FIGS. 1A and 1B that the dialysis machine is to be automatically powered on within a certain period of time and to provide the operator an opportunity to abort the automatic powering on process.

As discussed above, in certain cases, an alert that the machine is about to power on is displayed on the user interface of the hemodialysis machine 106. FIG. 11 shows one example of such an alert 1100 being displayed on the user interface 150 of the hemodialysis machine 106. The user interface 150 displays a timer notification that alerts the operators that the hemodialysis machine is powering on and allows a manual override of the automatic turning on. On the user interface the timer displays a countdown. The hemodialysis machine does not fully turn on until the timer has run down, thereby allowing the operator to clear the area. Additionally, if the alerts are patterned or pulsed, the frequency of an alert may increase with the expiration of time. In some embodiments, a long pulse occurs when the timer is close to expiring, for example the last five seconds of the countdown. During the countdown the user interface also displays an abort option in which the operator may abort the automatic powering on by touching the "Press to abort" button. The user may do this, for example, if the hemodialysis machine is not needed in the clinic or the hemodialysis machine requires maintenance.

Figure 12:
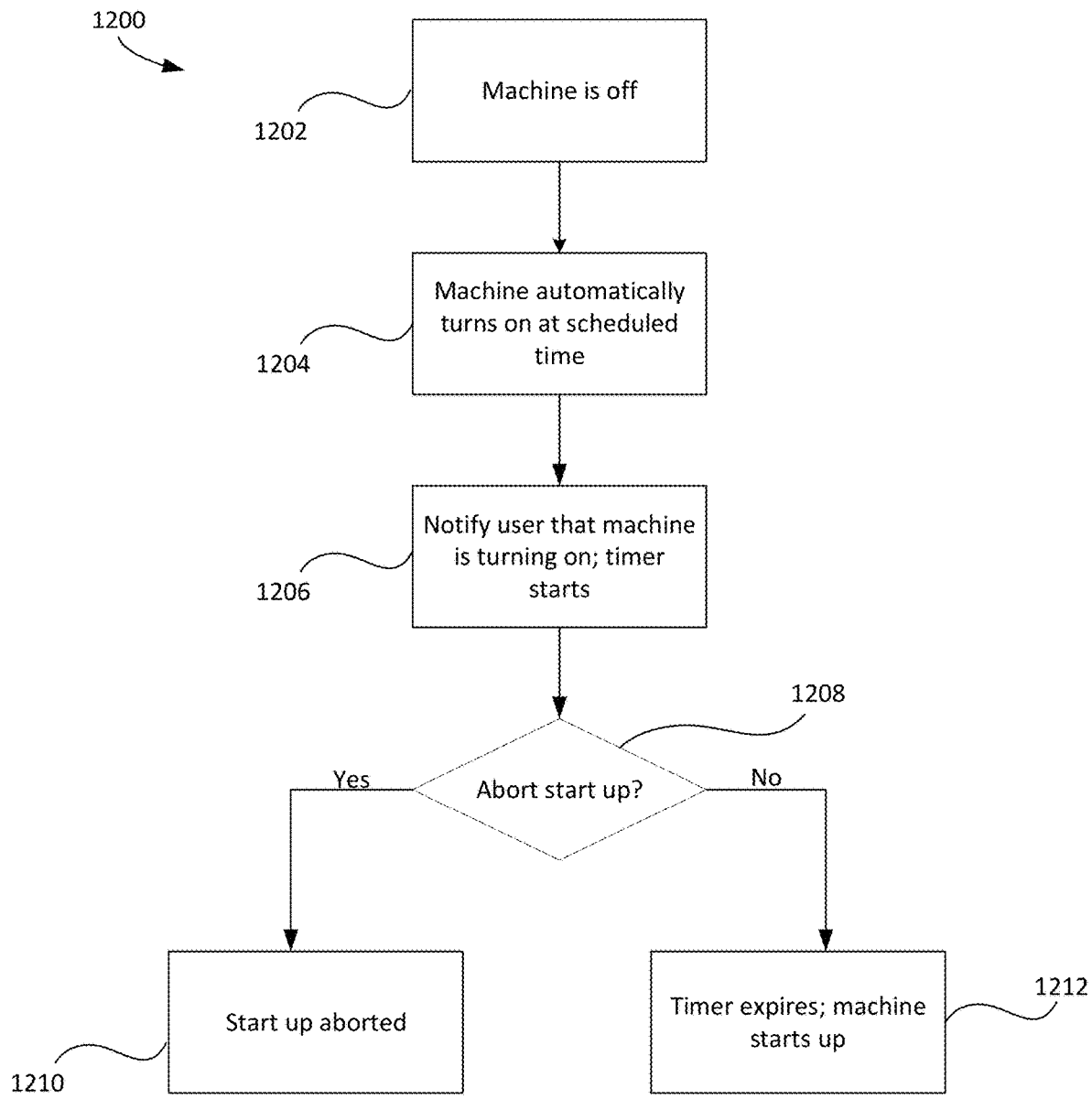
FIG. 12 is a flow chart illustrating a procedure for a hemodialysis machine that includes displaying a countdown timer and an abort option prior to automatically turning on the hemodialysis machine.

FIG. 12 shows a procedure 1200 for the automatic powering on of a hemodialysis machine, which includes displaying a countdown timer and an abort option. The hemodialysis machine is preprogrammed to turn on at a scheduled time. The device is initially powered off 1202 and begins to turn on at the scheduled time 1204. Prior to fully powering on, an alert notifies a user or operator around the hemodialysis machine that the hemodialysis machine is powering on and a timer is initiated 1206. The alert may be auditory, visual, vibrational, or a combination thereof. With the alert, a notification on the user interface displays a countdown of the timer and prompts an option for the user to abort the automatic start up 1208. The message may be similar to the message shown in FIG. 11. If the user confirms to abort the startup, the hemodialysis machine returns to a powered off mode 1210. If the user does not abort the startup, the timer expires and the hemodialysis machine continues with powering on 1212.

In some embodiments, the hemodialysis machine includes a safety circuit that is configured to allow at least some sensors to receive power and to prevent high voltage components from receiving power. The safety circuit for example may pass a small current that is sufficient to power the sensors, the user interface, and the controller, but is not large enough to power the pumps, the clamps, and other mechanical parts that require high voltage. This procedure checks the environment prior to powering high voltage components. For example, the safety circuit may include a sensor on the panel or door leading to the internal components of the hemodialysis machine, configured to sense if the door is opened or closed.

Other types of sensors can alternatively or additionally be used to determine whether conditions are safe for permitting the hemodialysis machine 106 to automatically power on. In some implementations, for example, the hemodialysis machine 106 is provided with a humidity sensor that can detect moisture on the machine. If the detected humidity level exceeds a threshold value, then the machine will not be allowed to automatically power on. This can help to prevent electrical shocks or other system malfunctions resulting from high moisture levels.

Figure 13:
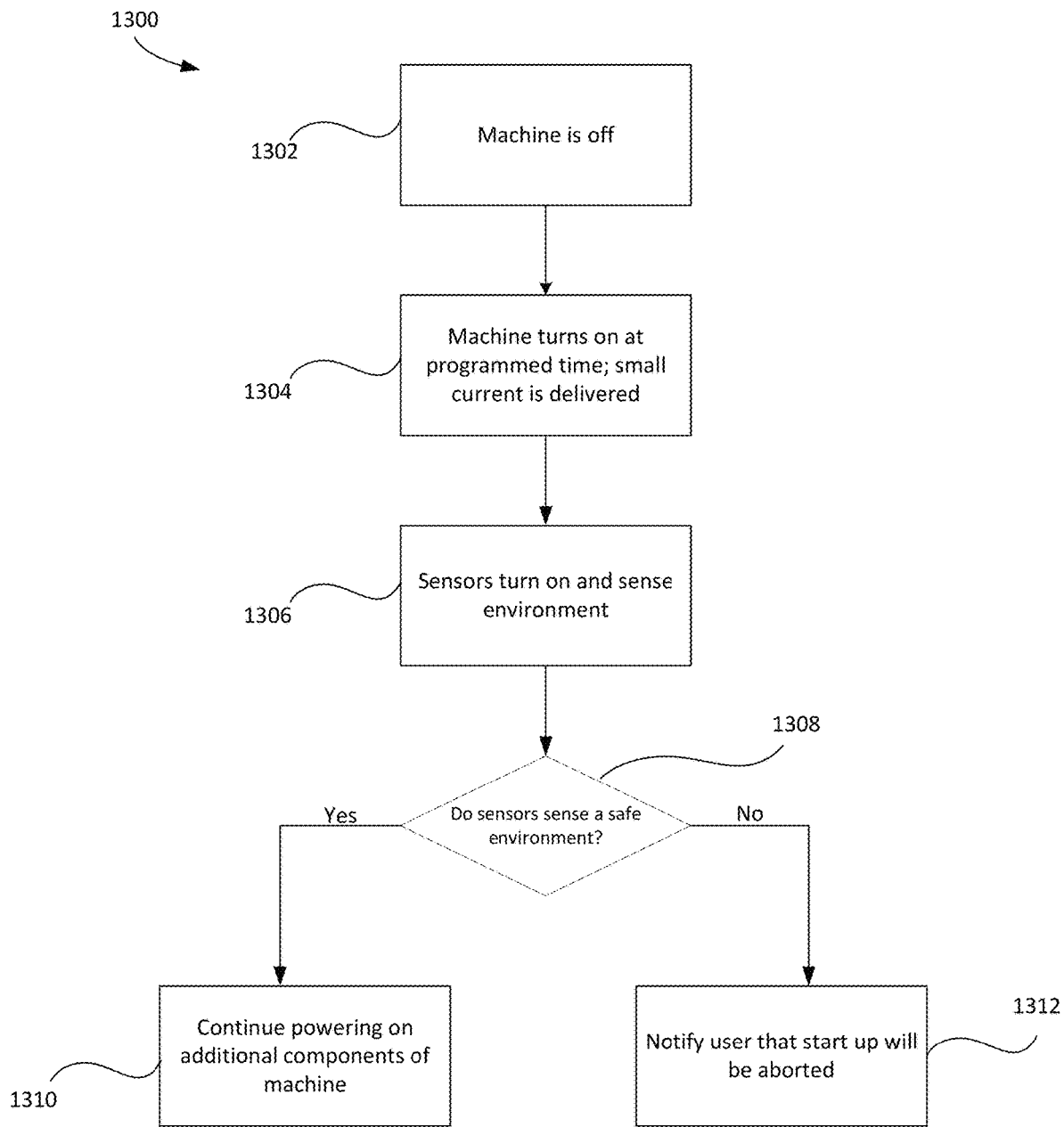
FIG. 13 is a flow chart illustrating a procedure for a hemodialysis machine that uses sensors of the hemodialysis machine to ensure the environment is safe prior to automatically turning on the hemodialysis machine.

FIG. 13 shows a procedure 1300 for a hemodialysis machine that uses sensors of the hemodialysis machine to test the environment prior to turning on. The hemodialysis is preprogrammed to turn on at a scheduled time. The device is initially powered off 1302 and begins to turn on at the scheduled time 1304. A small current is delivered to the sensors of the hemodialysis machine, the user interface, and the controller 1306. The current is not large enough to power high voltage components of the hemodialysis machine, such as pumps and clamps. The sensors sense the environment of the hemodialysis machine 1308, such as, the position of the doors of the hemodialysis machine. If the sensors determine that the environment is safe to turn on, the hemodialysis machine proceeds with powering on the high voltage components by delivering a higher current 1310. If the sensors determine that the environment is not safe to turn on, the hemodialysis machine will abort the automatic start up and will notify the user 1312. The aborting notification may include the reason for abortion. For example, the notification may note that the panel leading to internal components is open.

While methods of priming a blood line set of a hemodialysis system have been described, those priming methods can alternatively or additionally be used to prime the blood line sets of various other types of blood treatment systems, including hemofiltration systems, hemodiafiltration systems, ultrafiltration systems, therapeutic plasma exchange systems, etc.

While the hemodialysis system has been described as using a saline solution to prime the blood line set, any of various other suitable priming solutions could be used. In certain implementations, for example, dialysate is used to prime the blood line set.

While the flow regulators have been described as manual or automatic clamps, the flow regulators can be manually operable, electronically addressable, or both.

While the hemodialysis machine has been described as including an ultrafiltration pump to withdraw liquid from the blood in the extracorporeal blood circuit and into a waste line, the ultrafiltration pump is not required in certain embodiments.

While the user interface system has been described as being integral with the hemodialysis machine, in some implementations the user interface system may not be integral with the hemodialysis machine. In some examples, the user interface system may be wirelessly connected to the hemodialysis machine, e.g. the user interface system may be a tablet or other display device. In some examples, the user interface system may have a wired connection to the hemodialysis machine.

While the automatic priming system of the embodiments shown and discussed above includes automatic priming for a hemodialysis system with separable blood line sets, automatic priming can also be used with a cassette-style blood line set.

While the automatic priming system of the embodiments shown and described includes error messages in text form, error messages may be displayed to the user in a graphical form to indicate to the user which component of the hemodialysis machine needs to be addressed to remedy the error. Alternatively or additionally, audible error alarms may be emitted to indicate which component of the hemodialysis machine needs to be addressed to remedy the error.

While the pressure monitoring of the embodiments shown and discussed herein include monitoring for detecting errors for automatic priming, assisted reinfusion functions could also benefit from automatic pressure monitoring as performed herein.

The hemodialysis treatment systems described herein can be controlled, at least in part, using one or more computer program products, e.g., one or more computer programs tangibly embodied in one or more information carriers, such as one or more non-transitory machine-readable media, for execution by, or to control the operation of, one or more data processing apparatus, e.g., a programmable processor, a computer, multiple computers, and/or programmable logic components.

While the systems above have been described as hemodialysis systems, the various different automatic priming, scheduling, and alerting features discussed above can also be applied to other types of dialysis systems, including peritoneal dialysis systems.

While the systems above have been described as dialysis systems, the various systems discussed incorporating automatic power on and automatic diagnostic testing can also be applied to other medical devices, including medical drones or medical robots.

Operations associated with controlling the dialysis treatment systems described herein can be performed by one or more programmable processors executing one or more computer programs to perform the functions described herein. A computer program can be written in any form of programming language, including compiled or interpreted languages, and it can be deployed in any form, including as a stand-alone program or as a module, component, subroutine, or other unit suitable for use in a computing environment. Control over all or part of the dialysis treatment systems described herein can be implemented using special purpose logic circuitry, e.g., an FPGA (field programmable gate array) and/or an ASIC (application-specific integrated circuit).

The controllers described herein can include one or more processors. Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Machine-readable storage media suitable for embodying computer program instructions and data include all forms of nonvolatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Other implementations are within the scope of the claims.

The invention claimed is:

1. A method of operating a dialysis machine, the method comprising:

automatically emitting: (a) an alert comprising a visual notification on a user interface of the dialysis machine and (b) auditory alerts, to warn personnel in the vicinity of the dialysis machine that the dialysis machine is about to be automatically powered on, wherein the visual notification comprises displaying: (i) a countdown of an amount of time until the dialysis machine will be automatically powered on and (ii) an abort option button that an operator may select to abort the dialysis machine being automatically powered on;

in response to the countdown of the amount of time becoming close to expiring, increasing a frequency of the auditory alerts or a length of the auditory alerts;

in response to the countdown of the amount of time running down to expiration, automatically powering on the dialysis machine;

in response to the dialysis machine becoming powered on, automatically beginning and performing at least one integrity test on the dialysis machine, wherein the dialysis machine is programmed to automatically begin and perform the at least one integrity test in response to becoming powered on, and wherein the at least one integrity test is selected from the group consisting of a battery test, a dialysate conductivity test, and a dialysate temperature test; and presenting, on a display of the dialysis machine, a first set of instructions for priming the dialysis machine after completing the at least one integrity test.

2. The method of claim 1, comprising presenting, on the display, an instruction of the first set of instructions comprising flowing, using gravity, priming fluid from a fluid source through an arterial blood line set.

3. The method of claim 2, comprising presenting, on the display, an instruction of the first set of instructions comprising closing an end of the arterial blood line set and pumping the priming fluid through a dialyzer to prime the dialyzer.

4. The method of claim 2, comprising presenting, on the display, an instruction of the first set of instructions comprising priming a dialysate side of a dialyzer of the dialysis machine prior to priming the arterial blood line set.

5. The method of claim 1, comprising presenting, on the display of the dialysis machine, a second set of instructions for priming the dialysis machine upon completion of the first set of instructions.

6. The method of claim 5, wherein completion of the first set of instructions comprises running a predetermined volume of fluid through a blood pump.

7. The method of claim 5, wherein the second set of instructions is a set of instructions for a recirculation portion of an automatic priming procedure, wherein the second set of instructions instructs a user to connect the arterial blood line set to a venous blood line set.

8. The method of claim 7, wherein one instruction in the second set of instructions instructs a user to rotate a dialyzer.

9. The method of claim 7, comprising performing at least one functionality test during the recirculation portion of the automatic priming procedure, wherein the at least one functionality test is selected from the group consisting of a positive pressure test, a negative pressure test, an optical detection test, a blood leak detection test, a level detection test, a transmembrane pressure test, a venous pressure test, and an arterial pressure test.

10. The method of claim 7, wherein the first set of instructions is displayed on a first screen, wherein the second set of instructions is displayed on a second screen, the second screen replacing the first screen when the first set of instructions is completed, and wherein at least one of the first screen and the second screen comprises a progress bar for indicating progress of the priming process.

11. The method of claim 9, wherein performing at least one functionality test comprises:

measuring at least one parameter associated with the at least one functionality test;

comparing, by a controller, the at least one parameter to an expected operating range for the at least one parameter;

if the at least one parameter is outside of the expected operating range, returning an error message on the display; and if the at least one parameter is within the expected operating range, indicating, on the display, that the at least one functionality test has been passed, wherein the error message comprises a description of a problem with at least one component of the dialysis machine.

12. The method of claim 1, comprising presenting, on the display, a graphical representation of the dialysis machine, wherein the graphical representation of the dialysis machine and the first set of instructions include labels indicating that a step in the first set of instructions including the labels should be performed on a component of the dialysis machine including the labels.

13. The method of claim 1, further comprising automatically powering on the dialysis machine at a pre-set time on a selected day.

14. The method of claim 1, wherein the alert further comprises a vibrational alert.

15. The method of claim 1, wherein the visual notification further comprises one or more blinking lights located at a top of the dialysis machine.

16. The method of claim 1, wherein the amount of time is at least 10 seconds.

* * * * *